United States Patent [19]

Nelson

[11] 4,116,989

[45] Sep. 26, 1978

[54] 16-PHENOXY PROSTAGLANDIN $F_{1\alpha}$ ANALOGS

[75] Inventor: Norman A. Nelson, Galesburg, Mich.

[73] Assignee: The Upjohn Company, Kalamazoo, Mich.

[21] Appl. No.: 766,011

[22] Filed: Feb. 7, 1977

Related U.S. Application Data

[62] Division of Ser. No. 426,058, Dec. 19, 1973, which is a division of Ser. No. 252,030, May 10, 1972.

[51] Int. Cl.$^2$ ............................................. C07C 177/00
[52] U.S. Cl. ..................................... 260/413; 260/410; 260/410.5; 260/410.9 R; 260/408; 562/465; 560/55

[58] Field of Search .................. 260/410, 410.5, 410.9, 260/408, 520; 560/55

[56] References Cited

U.S. PATENT DOCUMENTS 4,024,179   5/1977   Bindra ..................................... 560/56

*Primary Examiner*—Paul J. Killos
*Attorney, Agent, or Firm*—Morris L. Nielsen

[57] ABSTRACT

Prostaglandin-type compounds with a phenoxy or substituted-phenoxy substituent at the C-16 position are disclosed, with processes for making them. These compounds are useful for a variety of pharmacological purposes, including anti-ulcer, inhibition of platelet aggregation, increase of nasal patency, labor inducement at term, and wound healing.

10 Claims, No Drawings

16-PHENOXY PROSTAGLANDIN $F_{1\alpha}$ ANALOGS

CROSS REFERENCE TO RELATED APPLICATIONS

This is a division of copending application Ser. No. 426,058 filed Dec. 19, 1973 which was a division of then copending application Ser. No. 252,030, filed May 10, 1972.

BACKGROUND OF THE INVENTION

This invention relates to novel compositions of matter, to novel methods for producing those, and to novel chemical intermediates useful in those processes. Particularly, this invention relates to certain novel analogs of some of the known prostaglandins in which there is a phenoxy or substituted-phenoxy substituent at the C-16 position, i.e. on the carbon atom adjacent to the hydroxy-substituted carbon in the methyl-terminated chain.

The known prostaglandins include, for example, prostaglandin $E_2$ (PGE$_2$), prostaglandin $F_2$ alpha and beta (PGF$_{2\alpha}$ and PGF$_{2\beta}$), prostaglandin $A_2$ (PGA$_2$), prostaglandin $B_2$ (PGB$_2$), and the corresponding PG$_1$ compounds. Each of the above-mentioned known prostaglandins is a derivative of prostanoic acid which has the following structure and atom numbering:

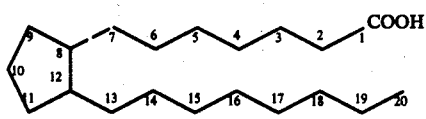

I

See, for example, Bergstrom et al., Pharmacol. Rev. 20, 1 (1968), and references cited therein. A systematic name for prostanoic acid is 7-[(2β-octyl)-cyclopent-1α-yl]-heptanoic acid.

PGE$_2$ has the following structure:

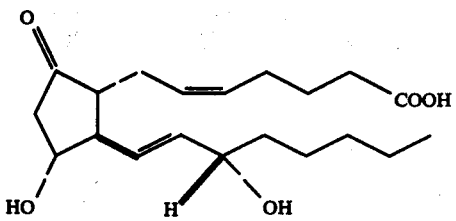

II

PGF$_{2\alpha}$ has the following structure:

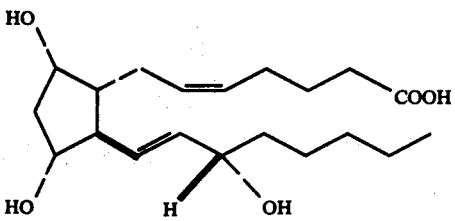

III

PGF$_{2\beta}$ has the following structure:

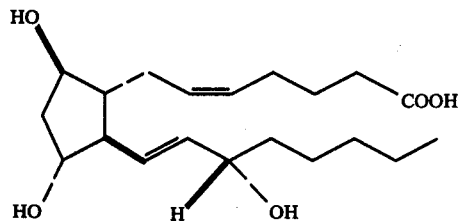

IV

PGA$_2$ has the following structure:

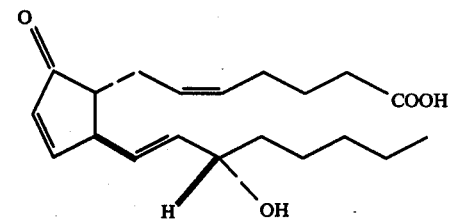

V

PGB$_2$ has the following structure:

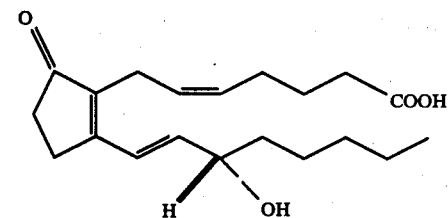

VI

Each of the known PG$_1$ prostaglandins, PGE$_1$, PGF$_{2\alpha}$, PGF$_{1\beta}$, PGA$_1$, and PGB$_1$, has a structure the same as that shown for the corresponding PG$_2$ compound except that, in each, the cis carbon-carbon double bond between C-5 and C-6 is replaced by a single bond. For example, PGE$_1$ has the following structure:

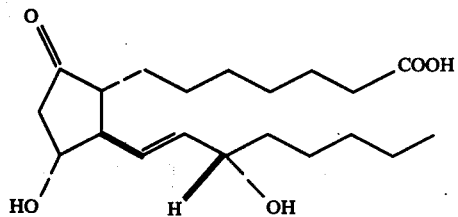

VII

In formulas II to VII, as well as in the formulas given hereinafter, broken line attachments to the cyclopentane ring indicate substituents in alpha configuration, i.e., below the plane of the cyclopentane ring. Heavy solid line attachments to the cyclopentane ring indicate substituents in beta configuration, i.e., above the plane of the cyclopentane ring.

Following the conventional numbering of the carbon atoms in the prostanoic acid structure, C-16 designates the carbon atom adjacent to the hydroxy-substituted carbon atom (C-15).

The side-chain hydroxy at C-15 in formulas II to VII is in S configuration. See, Nature, 212, 38 (1966) for discussion of the stereochemistry of the prostaglandins.

Molecules of the known prostaglandins each have several centers of asymmetry, and can exist in racemic (optically inactive) form and in either of the two enantiomeric (optically active) forms, i.e. the dextrorotatory and levorotatory forms. As drawn, formulas II to VII each represent the particular optically active form of the prostaglandin which is obtained from certain mammalian tissues, for example, sheep vesicular glands, swine lung, or human seminal plasma, or by carbonyl and/or double bond reduction of that prostaglandin. See, for example, Bergstrom et al., cited above. The mirror image of each of formulas II to VII represents the other enantiomer of that prostaglandin. The racemic form of a prostaglandin contains equal numbers of both enantiomeric molecules, and one of formulas II to VII and the mirror image of that formula is needed to represent correctly the corresponding racemic prostaglandin. For convenience hereinafter, use of the terms $PGE_1$, $PGE_2$, $PGE_3$, $PGF_{1\alpha}$, and the like, will mean the optically active form of that prostaglandin with the same absolute configuration as $PGE_1$ obtained from mammalian tissues. When reference to the racemic form of one of those prostaglandins is intended, the word "racemic" or "dl" will precede the prostaglandin name, thus, racemic $PGE_1$ or dl-$PGF_{2\alpha}$.

$PGE_1$, $PGE_2$, and the corresponding $PGF_\alpha$, $PGF_\beta$, PGA, and PGB compounds, and their esters, acylates, and pharmacologically acceptable salts, are extremely potent in causing various biological responses. For that reason, these compounds are useful for pharmacological purposes. See, for example, Bergstrom et al., cited above. A few of those biological responses are systemic arterial blood pressure lowering in the case of the $PGF_\beta$ and PGA compounds as measured, for example, in anesthetized (pentobarbital sodium) pentolinium-treated rats with indwelling aortic and right heart cannulas; pressor activity, similarly measured for the $PGF_\alpha$ compounds; stimulation of smooth muscle as shown, for example, by tests on strips of guinea pig ileum, rabbit duodenum, or gerbil colon; potentiation of other smooth muscle stimulants; antilipolytic activity as shown by antagonism of epinephrine-induced mobilization of free fatty acids or inhibition of the spontaneous release of glycerol from isolated rat fat pads; inhibition of gastric secretion in the case of the PGE and PGA compounds as shown in dogs with secretion stimulated by food or histamine infusion; activity on the central nervous system; controlling spasm and facilitating breathing in asthmatic conditions; decrease of blood platelet adhesiveness as shown by platelet-to-glass adhesiveness, and inhibition of blood platelet aggregation and thrombus formation induced by various physical stimuli, e.g., arterial injury, and various biochemical stimuli, e.g., ADP, ATP, serotonin, thrombin, and collagen; and in the case of the PGE nd PGB compounds, stimulation of epidermal proliferation and keratinization as shown when applied in culture to embryonic chick and rat skin segments.

Because of these biological responses, these known prostaglandins are useful to study, prevent, control, or alleviate a wide variety of diseases and undesirable physiological conditions in birds and mammals, including humans, useful domestic animals, pets, and zoological specimens, and in laboratory animals, for example, mice, rats, rabbits, and monkeys.

For example, these compounds, and especially the PGE compounds, are useful in mammals, including man, as nasal decongestants. For this purpose, the compounds are used in a dose range of about 10 μg. to about 10 mg. per ml. of a pharmacologically suitable liquid vehicle or as an aerosol spray, both for topical application.

The PGE, $PGF_\alpha$, and PGA compounds are useful in the treatment of asthma. For example, these compounds are useful as bronchodilators or as inhibitors of mediators, such as SRS-A, and histamine which are released from cells activated by an antigen-antibody complex. Thus, these compounds control spasm and facilitate breathing in conditions such as bronchial asthma, bronchitis, bronchiectasis, pneumonia and emphysema. For these purposes, these compounds are administered in a variety of dosage forms, e.g., orally in the form of tablets, capsules, or liquids; rectally in the form of suppositories; parenterally, subcutaneously, or intramuscularly, with intravenous administration being preferred in emergency situations; by inhalation in the form of aerosols or solutions for nebulizers; or by insufflation in the form of powder. Doses in the range of about 0.01 to 5 mg. per kg. of body weight are used 1 to 4 times a day, the exact dose depending on the age, weight, and condition of the patient and on the frequency and route of administration. For the above use these prostaglandins can be combined advantageously with other antiasthmatic agents, such as sympathomimetics (isoproterenol, phenylephrine, ephedrine, etc); xanthine derivatives (theophylline and aminophyllin); and corticosteroids (ACTH and predinisolone). Regarding use of these compounds see South African Pat. No. 68/1055.

The PGE and PGA compounds are useful in mammals, including man and certain useful animals, e.g., dogs and pigs, to reduce and control excessive gastric secretion, thereby reducing or avoiding gastrointestinal ulcer formation, and accelerating the healing of such ulcers already present in the gastrointestinal tract. For this purpose, the compounds are injected or infused intravenously, subcutaneously, or intramuscularly in an infusion dose range about 0.1 μg. to about 500 μg. per kg. of body weight per minute, or in a total daily dose by injection or infusion in the range about 0.1 to about 20 mg. per kg. of body weight per day, the exact dose depending on the age, weight, and condition of the patient or animal, and on the frequency and route of administration.

The PGE, $PGF_\alpha$, and $PGF_\beta$ compounds are useful whenever it is desired to inhibit platelet aggregation, to reduce the adhesive character of platelets, and to remove or prevent the formation of thrombi in mammals, including man, rabbits, and rats. For example, these compounds are useful in the treatment and prevention of myocardial infarcts, to treat and prevent post-operative thrombosis, to promote patency of vascular grafts following surgery, and to treat conditions such as atherosclerosis, arteriosclerosis, blood clotting defects due to lipemia, and other clinical conditions in which the underlying etiology is associated with lipid imbalance or hyperlipidemia. For these purposes, these compounds are administered systemically, e.g., intravenously, subcutaneously, intramuscularly, and in the form of sterile implants for prolonged action. For rapid response, especially in emergency situation, the intravenous route of administration is preferred. Doses in the range about 0.005 to about 20 mg. per kg. of body weight per day are used, the exact dose depending on the age, weight, and condition of the patient or animal, and on the frequency and route of administration.

The PGE, $PGF_\alpha$, and $PGF_\beta$ compounds are especially useful as additives to blood, blood products, blood substitutes, and other fluids which are used in artificial extracorporeal circulation and perfusion of isolated body portions, e.g., limbs and organs, whether attached to the original body, detached and being preserved or prepared for transplant, or attached to the new body. During these circulations and perfusions, aggregated platelets tend to block the blood vessels and portions of the circulation apparatus. This blocking is avoided by the presence of these compounds. For this purpose, the compound is added gradually or in single or multiple portions to the circulating blood, to the blood of the donor animal, to the perfused body portion, attached or detached, to the recipient, or to two or all of those at a total steady state dose of about 0.001 to 10 mg. per liter of circulating fluid. It is especially useful to use these compounds in laboratory animals, e.g., cats, dogs, rabbits, monkeys, and rats, for these purposes in order to develop new methods and techniques for organ and limb transplants.

PGE compounds are extremely potent in causing simulation of smooth muscle, and are also highly active in potentiating other known smooth muscle stimulators, for example, oxytocic agents, e.g., oxytocin, and the various ergot alkaloids including derivatives and analogs thereof. Therefore, $PGE_2$, for example, is useful in place of or in combination with less than usual amounts of these known smooth muscle stimulators, for example, to relieve the symptoms of paralytic ileus, or to control or prevent atonic uterine bleeding after abortion or delivery, to aid in expulsion of the placenta, and during the puerperium. For the latter purpose, the PGE compound is administered by intravenous infusion immediately after abortion or delivery at a dose in the range about 0.01 to about 50 μg. per kg. of body weight per minute until the desired effect is obtained. Subsequent doses are given by intravenous, subcutaneous, or intramuscular injection or infusion during puerperium in the range 0.01 to 2 mg. per kg. of body weight per day, the exact dose depending on the age, weight, and condition of the patient or animal.

The PGA and $PGF_\beta$ compounds are useful as hypotensive agents to reduce blood pressure in mammals, including man. For this purpose, the compounds are administered by intravenous infusion at the rate of about 0.01 to about 50 μg. per kg. of body weight per minute, or in single or multiple doses of about 25 to 500 μg. per kg. of body weight total per day.

The PGA compounds and derivatives and salts thereof increase the flow of blood in the mammalian kidney, thereby increasing volume and electrolyte content of the urine. For that reason, PGA compounds are useful in managing cases of renal disfunction, especially in cases of severely impaired renal blood flow, for example, the hepatorenal syndrome and early kidney transplant rejection. In cases of excessive or inappropriate ADH (antidiuretic hormone; vasopressin) secretion, the diuretic effect of these compounds is even greater. In anephretic states, the vasopressin action of these compounds is especially useful. Illustratively, the PGA compounds are useful to alleviate and correct cases of edema resulting, for example, from massive surface burns, and in the management of shock. For these purposes, the PGA compounds are preferably first administered in intravenous injection at a dose in the range 10 to 1000 μg. per kg. of body weight or by intraveneous infusion at a dose in the range 0.1 to 20 μg. per kg. of body weight per minute until the desired effect is obtained. Subsequent doses are given by intravenous, intramuscular, or subcutaneous injection or infusion in the range 0.05 to 2 mg. per kg. of body weight per day.

The PGE, $PGF_\alpha$, and $PGF_\beta$ compounds are useful in place of oxytocin to induce labor in pregnant female animals, including man, cows, sheep, and pigs, at or near term, or in pregnant animals with intrauterine death of the fetus from about 20 weeks to term. For this purpose, the compound is infused intravenously at a dose of 0.01 to 50 μg. per kg. of body weight per minute until or near the termination of the second stage of labor, i.e., expulsion of the fetus. These compounds are especially useful when the female is one of more weeks post-mature and natural labor has not started, or 12 to 60 hours after the membranes have ruptured and natural labor has not yet started. An alternative route of administration is oral.

The PGE, $PGF_\alpha$, and $PGF_\beta$ compounds are useful for controlling the reproductive cycle in ovulating female mammals, including humans and animals such as monkeys, rats, rabbits, dogs, cattle, and the like. By the term ovulating female mammals is meant animals which are mature enough to ovulate but not so old that regular ovulation has ceased. For that purpose $PGF_{2\alpha}$, for example, is administered systemically at a dose level in the range 0.01 mg. to about 20 mg. per kg. of body weight of the female mammal, advantageously during a span of time starting approximately at the time of ovulation and ending approximately at the time of menses or just prior to menses. Intravaginal and intrauterine are alternative routes of administration. Additionally, expulsion of an embryo or a fetus is accomplished by similar administration of the compound during the first third of the normal mammalian gestation period.

As mentioned above, the PGE compounds are potent antagonists of epinephrine-induced mobilization of free fatty acids. For this reason, this compound is useful in experimental medicine for both in vitro and in vivo studies in mammals, including man, rabbits, and rats, intended to lead to the understanding, prevention, symptom alleviation, and cure of diseases involving abnormal lipid mobilization and high free fatty acid levels, e.g., diabetes mellitus, vascular diseases, and hyperthyroidism.

The PGE and PGB compounds promote and accelerate the growth of epidermal cells and keratin in animals, including humans, useful domestic animals, pets, zoological specimens, and laboratory animals. For that reason, these compounds are useful to promote and accelerate healing of skin which has been damaged, for example, by burns, wounds, and abrasions, and after surgery. These compounds are also useful to promote and accelerate adherence and growth of skin autografts, especially small, deep (Davis) grafts which are intended to cover skinless areas by subsequent outward growth rather than initially, and to retard rejection of homografts.

For these purposes, these compounds are preferably administered topically at or near the site where cell growth and keratin formation is desired, advantageously as an aerosol liquid or micronized powder spray, as an isotonic aqueous solution in the case of wet dressings, or as a lotion, cream, or ointment in combination with the usual pharmaceutically acceptable diluents. In some instances, for example, when there is substantial fluid loss as in the case of extensive burns or skin loss due to other causes, systemic administration is advantageous, for example, by intravenous injection or infusion, separate or in combination with the usual infusions of blood, plasma, or substitutes thereof. Alternative routes of administration are subcutaneous or intramuscular near the site, oral, sublingual, buccal, rectal, or vaginal. The exact dose depends on such factors as the route of administration, and the age, weight, and condition of the subject. To illustrate, a wet dressing for topical application to second and/or third degree burns of skin area 5 to 25 square centimeters would advantageously involve use of an isotonic aqeous solution containing 1 to 500 μg./ml. of the PGB compound or several times that concentration of the PGE compound. Especially for topical use, these prostaglandins are useful in combination with antibiotics, for example, gentamycin, neomycin, polymyxin B, bacitracin, spectinomycin, and oxytetracycline, with other antibacterials, for example, mafenide hydrochloride, sulfadiazine, furazolium chloride, and nitrofurazone, and with corticoid steroids, for example, hydrocortisone, prednisolone, methylprednisolone, and fluprednisolone, each of those being used in the combination at the usual concentration suitable for its use alone.

SUMMARY OF THE INVENTION

It is a purpose of this invention to provide novel 16-phenoxy and 16-(substituted phenoxy) prostaglandin analogs in which there is variable chain length in the side chains. It is a further purpose to provide esters, lower alkanoates, and pharmacologically acceptable salts of said analogs. It is a further purpose to provide novel processes for preparing said analogs and esters. It is still a further purpose to provide novel intermediates useful in said processes.

The presently describe acids and esters of the 16-phenoxy and 16-(substituted phenoxy) prostaglandin analogs include compounds of the following formulas, and also the racemic compounds of each respective formula and the mirror image thereof:

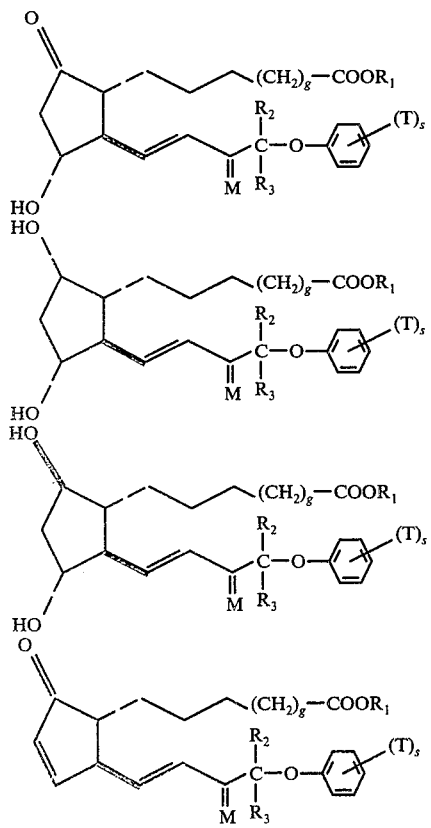

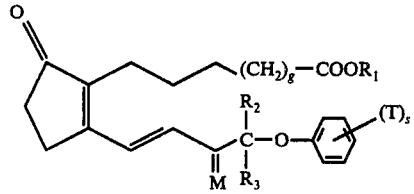

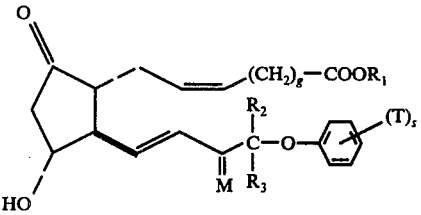

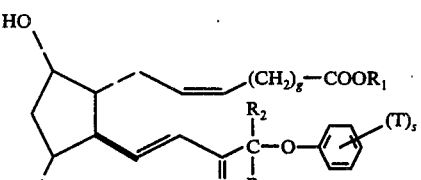

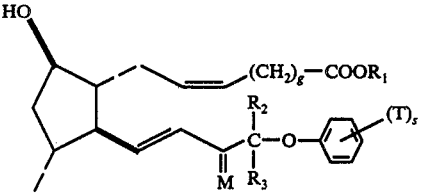

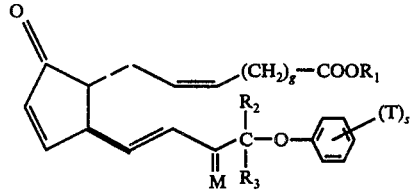

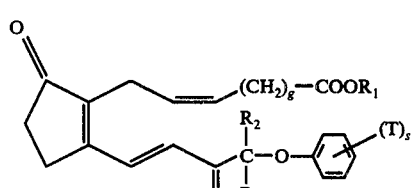

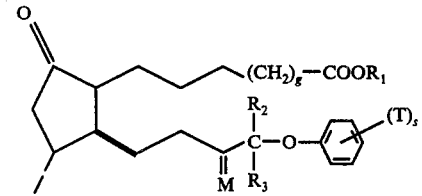

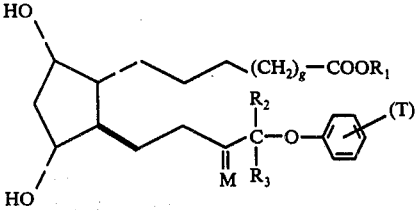

-continued

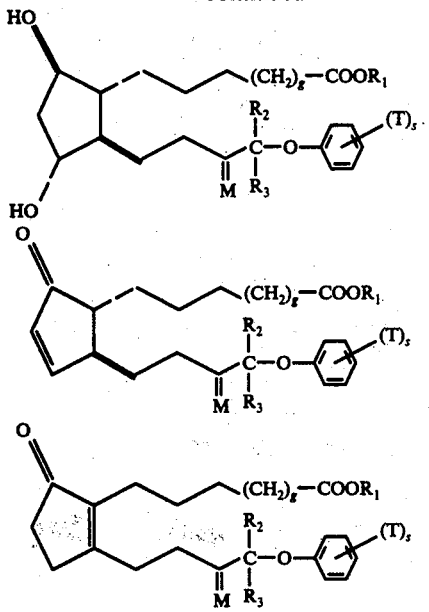

XX

XXI

XXII

In formulas VIII to XXII, g is an integer from 2 to 5, inclusive; M is

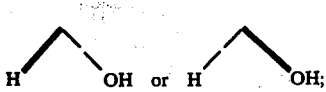

$R_1$ is hyrogen or alkyl of one to 12 carbon atoms, inclusive, cycloalkyl of 3 to 10 carbon atoms, inclusive, aralkyl of 7 to 12 carbon atoms, inclusive, phenyl, or phenyl substituted with one, 2, or 3 chloro or alkyl of one to 4 carbon atoms, inclusive; $R_2$ and $R_3$ are hydrogen, methyl, or ethyl; T is alkyl of one to 3 carbon atoms, inclusive, fluoro, chloro, trifluoro, or $-OR_4$ wherein $R_4$ is alkyl of one to 3 carbon atoms, inclusive; and s is zero, and 2, or 3, with the proviso that not more than two T's are other than alkyl. $R_2$ and $R_3$ may be the same or different.

Formula IX represents 16-phenoxy-18,19,20-trinor-$PGF_{1\alpha}$ when g is 3, M is

$R_1$ and $R_2$ are hydrogen, $R_3$ is methyl, and s is zero. Formula XIII represents 16-(2,4-dichlorophenoxy)-16-methyl-2a,2b-dihomo-18,19,20-trinor-$PGE_2$, methyl ester, when g is 5, M is

$R_1$, $R_2$, and $R_3$ are methyl, T is chloro, and s is 2. Formula XX represents 16-(4-fluoro-2,5-xylyloxy)-2,19,20-trinor-15β-13,14-dihydro-$PGF_{1\beta}$, dodecyl ester, when g is 2, M is

$R_1$ is dodecyl, $R_2$ is hydrogen, $R_3$ is ethyl, T is fluoro and methyl, and s is 3.

In the name of the formula-IX example above, "18,19,20-trinor" indicates absence of three carbon atoms from the hydroxy-substituted side chain of the $PGF_{1\alpha}$ structure. Following the atom numbering of the prostanoic acid structure, C-18, C-19, C-20 are construed as missing, and the methylene at C-17 is replaced with a terminal methyl group. Likewise, in the formula-XX example, "2,19,20-trinor" indicates the absence of the C-2 carbon atom from the carboxy-terminated side chain, and the C-19 and C-20 carbon atoms from the hyroxy-substituted side chain. In this system of nomenclature, the words "nor", "dinor", "trinor", "tetranor", or "pentanor" in the names of the prostaglandin analogs are to be construed as indicating one, two, three, four, or five carbon atoms, respectively, missing from the C-2 to C-4 and C-17 to C-20 positions of the prostanoic acid carbon skeleton.

In the name of the formula-XIII example, "2a,2b-dihomo" indicates two additional carbon atoms in the carboxy-terminated side chain specifically between the C-2 and C-3 carbon atoms. There are, therefore, nine carbon atoms in that side chain instead of the normal seven in the prostanoic acid structure. From the end of the chain to the double bond of the example they are identified as C-1, C-2, C-2a, C-2b, C-3, C-4, and C-5. The carbon atoms connected by the cis double bond are C-5 and C-6, and the carbon atoms between the double bond and the ring are C-6 and C-7.

As in the case of formulas II to VII, formulas VIII to XXII, wherein M is

i.e. wherein the hydroxyl is attached to the side chain in alpha configuration, are each intended to represent optically active prostanoic acid derivatives with the same absolute configuration as $PGE_1$ obtained from mammalian tissues.

Also included within this invention are the 15-epimer compounds of formulas VIII to XXII wherein M is

i.e. the C-15 hydroxyl is in beta configuration. Hereinafter "15β" refers to the epimeric configuration. Thus, "16-phenoxy-18,19,20-trinor-15β-$PGF_{1\alpha}$" identifies the 15-epimeric compound corresponding to the formula-IX example above except that it has the beta configuration at C-15 instead of the natural alpha configuration of 16-phenoxy-18,19,20-trinor-$PGF_{1\alpha}$.

Each of formulas VIII and XXII plus its mirror image describe a racemic compound within the scope of this invention. For convenience hereinafter, such a racemic compound is designated by the prefix "racemic" (or "dl") before its name; when that prefix is absent, the intent is to designate or optically active compound represented by the appropriate formula VIII to XXII.

With regard to formulas VIII to XXII, examples of alkyl of one to 12 carbon atoms, inclusive, are methyl, ethyl, propyl, butyl, pentyl, hexyl, heptyl, octyl, nonyl, decyl, undecyl, dodecyl, and isomeric forms thereof. Examples of cycloalkyl of 3 to 10 carbon atoms, inclusive, which includes alkyl-substituted cycloalkyl, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 2-pentylcyclopentyl, 3-tert-butylcyclopentyl, cyclohexyl, 4-tert-butylcyclohexyl, 3-isopropylcyclohexyl, 2,2-dimethylcyclohexyl, cycloheptyl, cyclooctyl, cyclononyl, and cyclodecyl. Examples of aralkyl of 7 to 12 carbon atoms, inclusive, are benzyl, phenethyl, 1-phenylethyl, 2-phenylpropyl, 4-phenylbutyl, 3-phenylbutyl, 2-(1-naphthylethyl), and 1-(2-naphthylmethyl). Examples of phenyl substituted by one to 3 chloro or alkyl of one to 4 carbon atoms, inclusive, are p-chlorophenyl, m-chlorophenyl, o-chlorophenyl, 2,4-dichlorophenyl, 2,4,6-trichlorophenyl, p-tolyl, o-tolyl, p-ethylphenyl, p-tert-butylphenyl, 2,5-dimethylphenyl, 4-chloro-2-methylphenyl, and 2,4-dichloro-3-methylphenyl.

Examples of

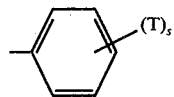

as defined above are phenyl, (o-, m-, or p-)tolyl, (o-, m-, or p-)ethylphenyl, 2-ethyl-p-tolyl, 4-ethyl-o-tolyl, 5-ethyl-m-tolyl, (o-, m-, or p-)propylphenyl, 2-propyl-(o-, m-, p-)tolyl, 4-isopropyl-2,6-xylyl, 3-propyl-4-ethylphenyl, (2,3,4-, 2,3,5-, 2,3,6-, or 2,4,5-)trimethylphenyl, (o-, m-, or p-)fluorophenyl, 2-fluoro-(o-, m-, or p-)tolyl, 4-fluoro-2,5-xylyl, (2,4-, 2,5-, 2,6-, 3,4-, or 3,5-)difluorophenyl, (o-, m-, or p-)-chlorophenyl, 2-chloro-p-tolyl, (3-, 4-, 5-, or 6-)chloro- o-tolyl, 4-chloro-2-propylphenyl, 2-isopropyl-4-chlorophenyl, 4-chloro-3,5-xylyl, (2,3-, 2,4-, 2,5-, 2,6-, 3,4-, or 3,5-)dichlorophenyl, 4-chloro-3-fluorophenyl, (3-, or 4-)chloro-2-fluorophenyl, α,α,α-trifluoro-(o-, m-, or p-)-tolyl, (o-, m-, or p-)methoxyphenyl, (o-, m-, or p-)ethoxyphenyl, (4- or 5-)chloro-2-methoxyphenyl, and 2,4-dichloro-(5- or 6-)methoxyphenyl.

Accordingly, there is provided an optically active compound of the formula

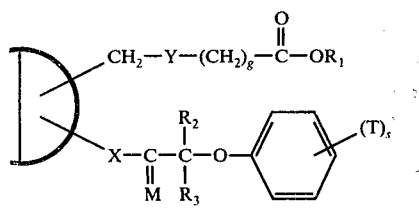

or a racemic compound of that formula and the mirror image thereof, wherein D is one of the four carbocyclic moieties:

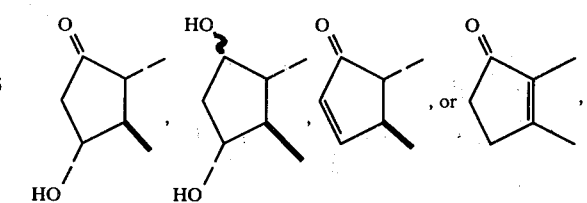

wherein ~ indicates attachment of hydroxyl to the ring in alpha or beta configuration; wherein (a) X is trans—CH=CH— or —CH$_2$CH$_2$—, and Y is —CH$_2$CH$_2$—, or (b) X is trans—CH=CH— and Y is cis—CH=CH—; wherein g is an integer from 2 to 5, inclusive; wherein M is

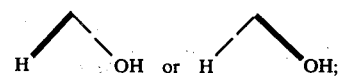

wherein R$_1$ is hydrogen or alkyl of one to 12 carbon atoms, inclusive, cycloalkyl of 3 to 10 carbon atoms, inclusive, aralkyl of 7 to 12 carbon atoms, inclusive, phenyl, or phenyl substituted with one, 2, or 3 chloro or alkyl of one to 4 carbon atoms, inclusive; wherein R$_2$ and R$_3$ are hydrogen, methyl, or ethyl; wherein T is alkyl of one to 3 carbon atoms, inclusive, fluoro, chloro, trifluoro, or —OR$_4$ wherein R$_4$ is alkyl of one to 3 carbon atoms, inclusive, and wherein s is zero, one, 2, or 3, with the proviso that not more than two T's are other than alkyl; including the lower alkanoates thereof, and the pharmacologically acceptable salts thereof when R$_1$ is hydrogen.

Formula XXIII, which is written in generic form for convenience, represents PGE-type compounds when D is

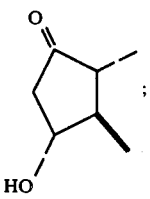

PGF$_α$-type compounds when D is

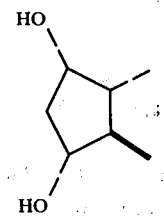

PGF$_β$-type compounds when D is

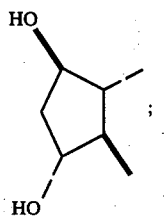

PGA-type compounds when D is

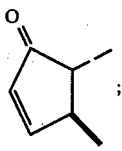

and PGB-type compounds when D is

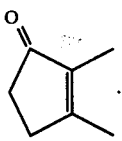

The novel formula VIII-to-XXIII compounds and the racemic compounds of this invention each cause the biological responses described above for the PGE, $PGF_\alpha$, $PGF_\beta$, PGA, and PGB compounds, respectively, and each of these novel compounds is accordingly useful for the above-described corresponding purposes, and is used for those purposes in the same manner as described above.

The known PGE, $PGF_\alpha$, $PGF_\beta$, PGA, and PGB compounds are all potent in causing multiple biological responses even at low doses. For example, $PGE_1$ and $PGE_2$ both cause vasodepression and smooth muscle stimulation at the same time they exert antilipolytic activity. Moreover, for many applications, these known prostaglandins have an inconveniently short duration of biological activity. In striking contrast, the novel prostaglandin analogs of formulas VIII to XXIII and their racemic compounds are substantially more specific with regard to potency in causing prostaglandin-like biological responses, and have a substantially longer duration of biological activity. Therefore, each of these novel prostaglandin analogs is surprisingly and unexpectedly more useful than one of the corresponding above-mentioned known prostaglandins for at least one of the pharmacological purposes indicated above for the latter, because it has a different and narrower spectrum of biological potency than the known prostaglandin, and therefore is more specific in its activity and causes smaller and fewer undesired side effects than when the known prostaglandin is used for the same purpose. Moreover, because of its prolonged activity, fewer and smaller doses of the novel prostaglandin analog can frequently be used to attain the desired result.

To obtain the optimum combination of biological response specificity, potency, and duration of activity, certain compounds within the scope of formulas VIII to XXIII are preferred. For example, it is preferred that the hydroxyl at C-15 be in the alpha configuration.

Another preference is that g be 3, i.e. that the carboxy-terminated side chain contain 7 carbon atoms.

Another preference is that substitution on the phenoxy be in the para position, at least.

Still another preference is that $R_2$ and $R_3$ be hydrogen or methyl. Both can be hydrogen, both can be methyl, or one can be hydrogen and the other methyl. When only one is methyl, C-16 is an asymmetric carbon atom and two isomeric forms exist with respect to the stereochemistry at C-16. That isomer is preferred, for the purposes described herein, which has the greater desired biological activity when subjected to tests known in the art. For example, smooth muscle stimulation is indicated in smooth muscle strip tests (see J. R. Weeks et al., Journal of Applied Physiology 25, (No. 6), 783 (1968); and antisecretory activity is indicated in in vivo tests with laboratory animals (see A. Robert, "Antisecretory Property of Prostaglandins," Prostaglandin Symposium of the Worcester Foundation for Experimental Biology, Interscience, 1968, pp. 47–54).

Another advantage of the novel compounds of this invention, expecially the preferred compounds defined hereinabove, compared with the known prostaglandins, is that these novel compounds are administered effectively orally, sublingually, intravaginally, buccally, or rectally, in addition to usual intravenous, intramuscular, or subcutaneous injection or infusion methods indicated above for the uses of the known prostaglandins. These qualities are advantageous because they facilitate maintaining uniform levels of these compounds in the body with fewer, shorter, or smaller doses, and make possible self-administration by the patient.

The 16-phenoxy and 16-(substituted phenoxy) PGE, $PGF_\alpha$, $PGF_\beta$, PGA, and PGB-type analogs encompassed by Formulas VIII to XXIII including their alkanoates, are used for the purposes described above in the free acid form, in ester form, or in pharmacologically acceptable salt form. When the ester form is used, the ester is any of those within the above definition of $R_1$. However, it is preferred that the ester be alkyl of one to 12 carbon atoms, inclusive. Of those alkyl, methyl and ethyl are especially preferred for optimum absorption of the compound by the body or experimental animal system; and straight-chain octyl, nonyl, decyl, undecyl, and dodecyl are especially preferred for prolonged activity in the body or experimental animal.

Pharmacologically acceptable salts of these Formula VIII-to-XXIII compounds useful for the purposes described above are those with pharmacologically acceptable metal cations, ammonium, amine cations, or quaternary ammonium cations.

Especially preferred metal cations are those derived from the alkali metals, e.g., lithium, sodium and potassium, and from the alkaline earth metals, e.g., magnesium and calcium, although cationic forms of other metals, e.g., aluminum, zinc, and iron are within the scope of this invention.

Pharmacologically acceptable amine cations are those derived from primary, secondary, or tertiary amines. Examples of suitable amines are methylamine, dimethylamine, trimethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and like aliphatic, cycloaliphatic, and aralphatic amines containing up to and including about 18 carbon atoms, as well as heterocyclic amines, e.g., piperidine, morpholine, pyrrolidine, piperazine, and lower-alkyl derivatives thereof, e.g., 1-methylpiperidine, 4-ethylmorpholine, 1-isopropylpyrrolidine, 2-methylpyrrolidine, 1,4-dimethylpiperazine, 2-methylpiperidine, and the like, as well as amines containing water-solubilizing or hydrophilic groups, e.g., mono-, di-, and triethanolamine, ethyldiethanolamine, N-butylethanolamine, 2-amino-1-butanol, 2-amino-2-ethyl-1,3-propanediol, 2-amino-2-methyl-1-propanol, tris(hydroxymethyl)aminomethane, N-phenylethanolamine, N-(p-tert-amylphenyl)diethanolamine, galactamine, N-methylglycamine, N-methylglucosamine, ephedrine, phenylephrine, epinephrine, procaine, and the like.

Examples of suitable pharmacologically acceptable quaternary ammonium cations are tetramethylammonium, tetraethylammonium, benzyltrimethylammonium, phenyltriethylammonium, and the like.

The compounds encompassed by Formulas VIII to XXIII are used for the purposes described above in free hydroxy form or also in the form wherein the hydroxy moieties are transformed to lower alkanoate moieties, e.g., —OH to —OCOCH$_3$. Examples of lower alkanoate moieties are acetoxy, propionyloxy, butyryloxy, valeryloxy, hexanoyloxy, heptanoyloxy, octanoyloxy, and branched chain alkanoyloxy isomers of those moieties. Especially preferred among these alkanoates for the above described purposes are the acetoxy compounds. These free hydroxy and alkanoyloxy compounds are used as free acids, as esters, and in salt form all as described above.

As discussed above, the compounds of Formulas VIII to XXIII are administered in various ways for various purposes; e.g., intravenously, intramuscularly, subcutaneously, orally, intravaginally, rectally, buccally, sublingually, topically, and in the form of sterile implants for prolonged action. For intravenous injection or infusion, sterile aqueous isotonic solutions are preferred. For that purpose, it is preferred because of increased water solubility that R$_1$ in the formula VIII-to-XXIII compound be hydrogen or a pharmacologically acceptable cation. For subcutaneous or intramuscular injection, sterile solutions or suspensions of the acid, salt, or ester form in aqueous or non-aqueous media are used. Tablets, capsules, and liquid preparations such as syrups, elixirs, and simple solutions, with the usual pharmaceutical carriers are used for oral sublingual administration. For rectal or vaginal administration, suppositories prepared as known in the art are used. For tissue implants, a sterile tablet or silicone rubber capsule or other object containing or impregnated with the substance is used.

The 16-phenoxy and 16-(substituted phenoxy) PGE-, PGF$_\alpha$-, PGF$_\beta$-, PGA-, and PGB-type analogs encompassed by formulas VIII to XXIII are produced by the reactions and procedures described and exemplified hereinafter.

Reference to Charts A and B herein, will make clear the steps for preparing the formula-XXIV through XXXIV intermediates.

Previously, the preparation of an intermediate bicyclic lactone diol of the formula

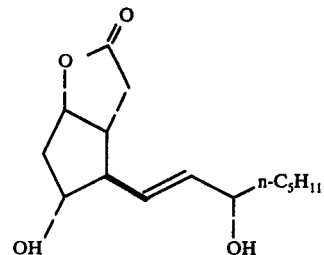

was reported by E. J. Corey et al., J. Am. Chem. Soc. 91, 5675 (1969), and later disclosed in an optically active form by E. J. Corey et al., J. Am. Chem. Soc. 92, 397 (1970). Conversion of this intermediate to PGE$_2$ and PGF$_{2\alpha}$, either in racemic or optically active form, was disclosed in those publications.

CHART A

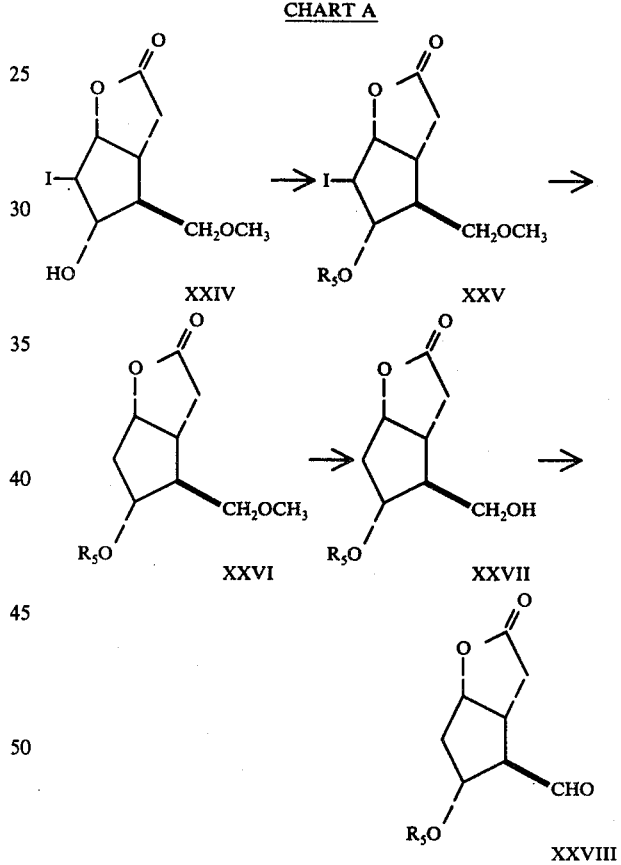

CHART B

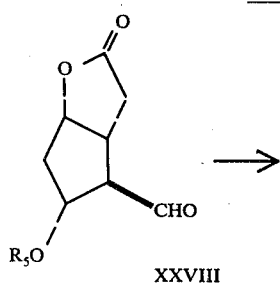

-continued
CHART B

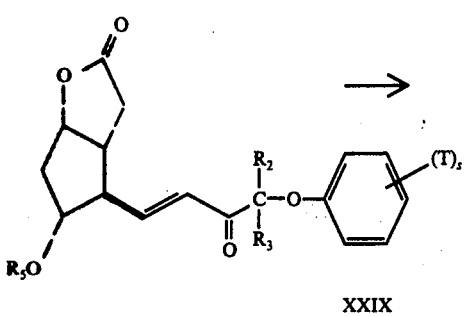

XXIX

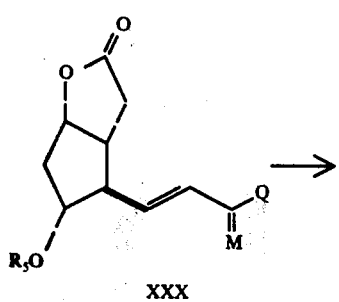

XXX

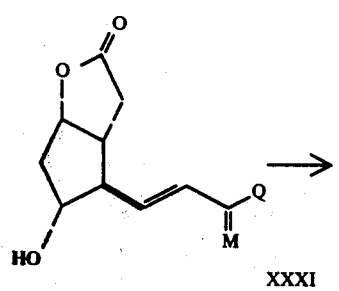

XXXI

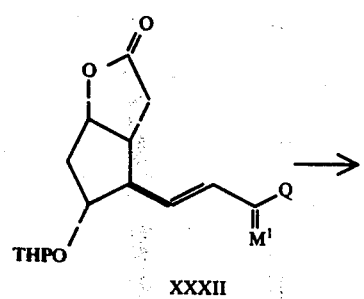

XXXII

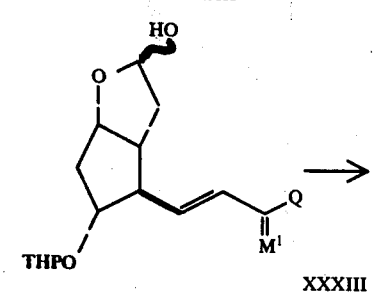

XXXIII

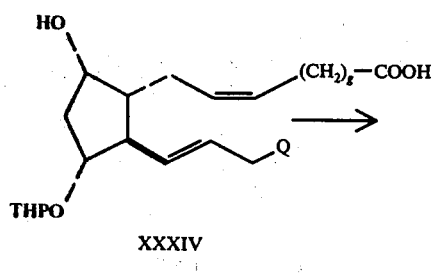

XXXIV

-continued
CHART B

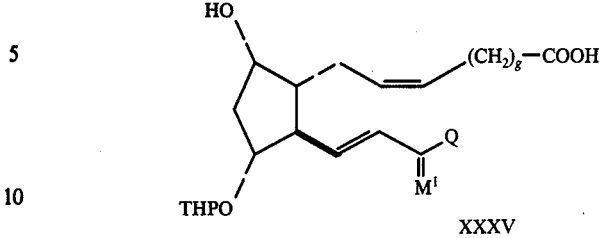

XXXV

The iodolactone of formula XXIV in Chart A is known in the art (see Corey et al., above). It is available in either racemic or optically active (+ or −) form. For racemic products, the racemic form is used. For prostaglandins of natural configuration, the laevorotatory form (−) is used.

In Charts A and B, $g$, M, $R_2$, $R_3$, T, and $s$ have the same meanings as defined above, namely: $g$ is an integer from 2 to 5, inclusive; M is

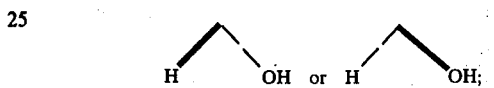

$R_2$ and $R_3$ are hydrogen, methyl, or ethyl, T is alkyl of one to 3 carbon atoms, inclusive, fluoro, chloro, trifluoromethyl, or $OR_4$ wherein $R_4$ is alkyl of one to 3 carbon atoms, inclusive, and $s$ is zero, one, 2, or 3, with the proviso that not more than two T's are other than alkyl. In addition, M' is

THP is tetrahydropyranyl; Q is

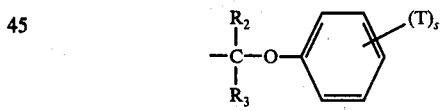

wherein $R_2$, $R_3$, T, and $s$ are as defined above; and ∼ represents attachment of hydroxy in alpha or beta configuration.

The formula-XXV compound (Chart A) bears an $R_5O-$ moiety at the 4-position, wherein $R_5$ is

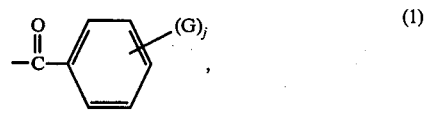   (1)

wherein G is alkyl of one to 3 carbon atoms, inclusive, phenylalkyl of 7 to 10 carbon atoms, inclusive, or nitro, and $j$ is zero to 5, inclusive, provided that not more than two G's are other than alkyl, and that the total number of carbon atoms in the G's does not exceed 10 carbon atoms;

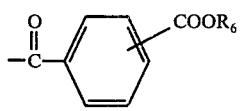 (2)

wherein $R_6$ is alkyl of one to 4 carbon atoms, inclusive;

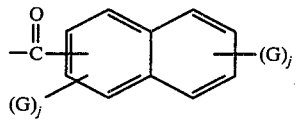 (3)

wherein G and $j$ are as defined above; or (4) acetyl. In preparing the formula-XXV compound by replacing the hydrogen of the hydroxyl group in the 4-position with the acyl group $R_5$, methods known in the art are used. Thus, an aromatic acid of the formula $R_5OH$, wherein $R_5$ is as defined above, for example benzoic acid, is reacted with the formula-XXIV compound in the presence of a dehydrating agent, e.g. sulfuric acid, zinc chloride, or phosphoryl chloride; or an anhydride of the aromatic acid of the formula $(R_5)_2O$, for example benzoic anhydride, is used.

Preferably, however, an acyl halide, $R_5Cl$, for example benzoyl chloride, is reacted with the formula-XXIV compound in the presence of a hydrogen chloride-scavenger, e.g. a tertiary amine such as pyridine, triethylamine, and the like. The reaction is carried out under a variety of conditions using procedures generally known in the art. Generally, mild conditions are employed, e.g. 20°-60° C., contacting the reactants in a liquid medium, e.g. excess pyridine or an inert solvent such as benzene, toluene or chloroform. The acylating agent is used either in stoichiometric amount or in excess.

The following examples of $R_5$ are available as acids $(R_5OH)$, anhydrides $((R_5)_2O)$, or acyl chlorides $(R_5Cl)$: benzoyl; substituted benzoyl, e.g. (2-, 3- or 4-)methylbenzoyl, (2-, 3-, or 4-)ethylbenzoyl, (2-, 3-, or 4-)isopropylbenzoyl, 2,4-dimethylbenzoyl, 3,5-dimethylbenzoyl, 2-isopropyltoluyl, 2,4,6-trimethylbenzoyl, pentamethylbenzoyl, α-phenyl-(2-, 3-, or 4-)toluyl, (2-, 3-, or 4-)phenethylbenzoyl, 2-, 3-, or 4-nitrobenzoyl, (2,4- 2,5- or 3,5-)dinitrobenzoyl, 3,4-dimethyl-2-nitrobenzoyl, 4,5-dimethyl-2-nitrobenzoyl, 2-nitro-6-phenethylbenzoyl, 3-nitro-2-phenethylbenzoyl; mono-esterified phthaloyl, e.g.

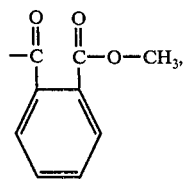

isophthaloyl, e.g.

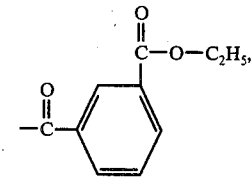

or terephthaloyl, e.g.

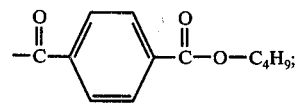

(1- or 2-)naphthoyl; substituted naphthoyl, e.g. (2-, 3-, 4-, 5-, 6-, or 7-)methyl-1-naphthoyl, (2- or 4-)ethyl-1-naphthoyl, 2-isopropyl-1-naphthoyl, 4,5-dimethyl-1-naphthoyl, 6-isopropyl-4-methyl-1-naphthoyl, 8-benzyl-1-naphthoyl, (3-, 4-, 5-, or 8-)nitro-1-naphthoyl, 4,5-dinitro-1-naphthoyl, (3-, 4-, 6-, 7-, or 8-)methyl-1-naphthoyl, 4-ethyl-2-naphthoyl, and (5- or 8-)nitro-2-naphthoyl; and acetyl. There may be employed, therefore, benzoyl chloride, 4-nitrobenzoyl chloride, 3,5-dinitrobenzoyl chloride, and the like, i.e. $R_5Cl$ compounds corresponding to the above $R_5$ groups. If the acyl chloride is not available, it is made from the corresponding acid and phosphorus pentachloride as is known in the art. It is preferred that the $R_5OH$, $(R_5)_2O$, or $R_5Cl$ reactant does not have bulky, hindering substituents, e.g. tert-butyl, on both of the ring carbon atoms adjacent to the carbonyl attaching-site.

The formula-XXVI compound is next obtained by deiodination of XXV using a reagent which does not react with the lactone ring or the $OR_5$ moiety, e.g. zinc dust, sodium hydride, hydrazine-palladium, hydrogen and Raney nickel or platinum, and the like. Especially preferred is tributyltin hydride in benzene at about 25° C. with 2,2'-azobis(2-methylpropionitrile) as initiator.

The formula-XXVII compound is obtained by demethylation of XXVI with a reagent that does not attack the $OR_5$ moiety, for example boron tribromide or trichloride. The reaction is carried out preferably in an inert solvent at about 0°-5° C.

The formula-XXVIII compound is obtained by oxidation of the —$CH_2OH$ of XXVII to —CHO, avoiding decomposition of the lactone ring. Useful for this purpose are dichromatesulfuric acid, Jones reagent, lead tetraacetate, and the like. Especially preferred is Collins' reagent (pyridine-$CrO_3$) at about 0°-10° C.

The formula-XXIX compound is obtained by Wittig alkylation of XXXI, using the sodio derivative of the appropriate 2-oxo-3-phenoxy (or 3-substituted phenoxy)-alkylphosphonate. The trans enone lactone is obtained stereospecifically (see D. H. Wadsworth et al., J. Org. Chem. Vol. 30, p. 680 (1965)).

In preparing the formula-XXIX compounds of Chart B, certain phosphonates are employed in the Wittig reaction. These are of the general formula

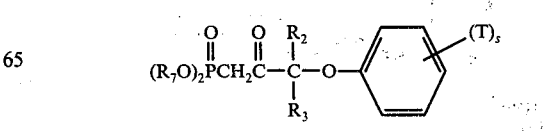

wherein $R_2$ and $R_3$ are hydrogen, methyl, or ethyl, being the same or different; $R_7$ is alkyl of one to 8 carbon atoms, inclusive; T is alkyl of one to 3 carbon atoms, inclusive, fluoro, chloro, trifluoro, or —$OR_4$ wherein $R_4$ is alkyl of one to 3 carbon atoms, inclusive, and s is zero, one, 2, or 3, with the proviso that not more than two T's are other than alkyl.

As examples of phosphonates useful for this purpose there are:

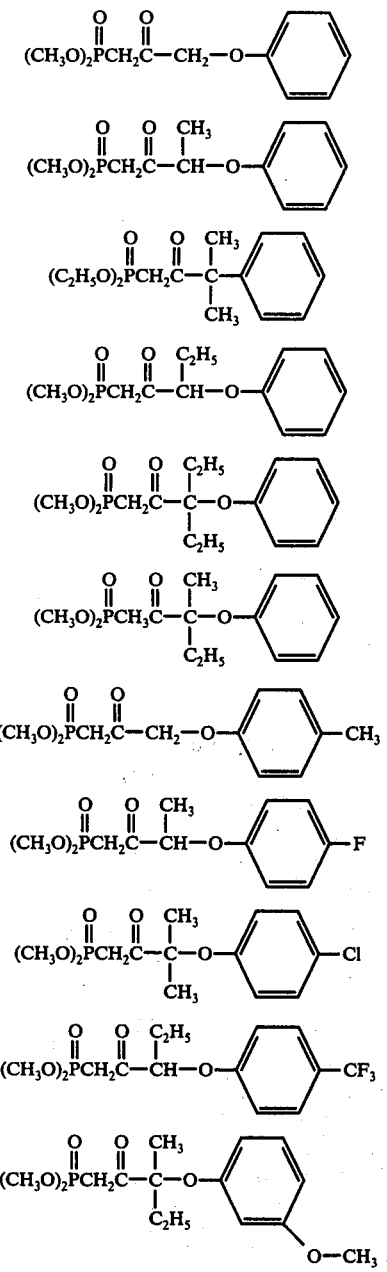

The phosphonates are prepared and used by methods known in the art. See Wadsworth et al., reference cited above. Conveniently, the appropriate aliphatic acid ester is condensed with the anion of dimethyl methylphosphonate produced by n-butyllithium. For this purpose, acids of the general formula

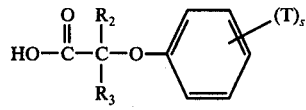

are used in the form of their lower alkyl esters, preferably methyl or ethyl. The methyl esters, for example, are readily formed from the acids by reaction with diazomethane. These aliphatic acids of various chain length, with phenoxy or substituted-phenoxy substitution within the scope of

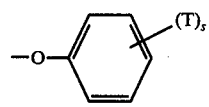

as defined above are known in the art or can be prepared by methods known in the art.

Many phenoxy-substituted acids are readily available, e.g. where $R_2$ and $R_3$ are both hydrogen: phenoxy-, (o-, m-, or p-)tolyloxy-, (o-, m-, or p-)ethylphenoxy-, 4-ethyl-o-tolyloxy-, (o-, m-, or p-)propylphenoxy-, (o-, m-, or p-)-t-butylphenoxy-, (o-, m-, or p-)fluorophenoxy-, 4-fluoro-2,5-xylyloxy-, (o-, m-, or p-)chlorophenoxy-, (2,3-, 2,4-, 2,5-, 2,6-, 3,4-, or 3,5-)dichlorophenoxy-, α,α,α-trifluoro-(o-, m-, or p-)tolyloxy-, or (o-, m-, or p-)methoxyphenoxyacetic acid; where $R_2$ is methyl and $R_3$ is hydrogen: 2-phenoxy-, 2-(o-, m-, or p-)tolyloxy-, 2-(3,5-xylyloxy)-, 2-(p-fluorophenoxy)-, 2-[o-, m-, or p-)chlorophenoxy]-, 2-[2,3-, 2,4-, 2,5-, 2,6-, 3,4-, or 3,5-)dichlorophenoxy]-, 2-[(4- or 6-)chloro-o-tolyloxy)-, or 2-(α,α,α-trifluoro-m-tolyloxy)propionic acid; wherein $R_2$ and $R_3$ are both methyl: 2-methyl-2-phenoxy-, 2-[(o-, m-, or p-)chlorophenoxy]-2-methyl-, or 2-[(2,3-, 2,4-, 2,5-, 2,6-, 3,4-, or 3,5-)dichlorophenoxy]-2-methylpropionic acid; where $R_2$ is ethyl and $R_3$ is hydrogen: 2-phenoxy-, 2-[(o-, m-, or p-)fluorophenoxy]-, 2-[(o-, m-, or p-)chlorophenoxy]-, 2-[(2,3-, 2,4-, 2,5-, 2,6-, 3,4-, or 3,5-)dichlorophenoxy]-, or 2-(2-chloro-4-fluorophenoxy)butyric acid; where $R_2$ is ethyl and $R_3$ is methyl: 2-methyl-2-phenoxy- or 2-[(o-, m-, or p-)chlorophenoxy]-2-methylbutyric acid.

Other phenoxy substituted acids are available by methods known in the art, for example, by the Williamson synthesis of ethers using an alpha-halo aliphatic acid or ester with sodium phenoxide or a substituted sodium phenoxide. Thus, the methyl ester of 2-(o-methoxyphenoxy)-2-methylbutyric acid is obtained by the following reaction:

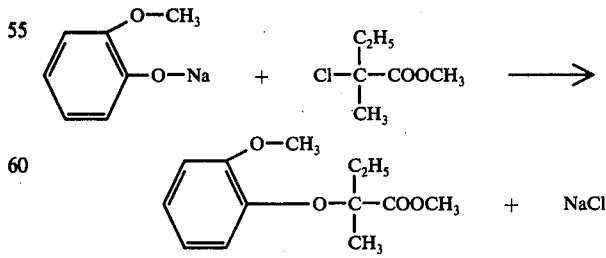

The reaction proceeds smoothly with heating and the product is recovered in the conventional way. The methyl ester is used for preparing the corresponding phosphonate as discussed above.

Alternatively, the phosphonate is prepared from an aliphatic acyl halide and the anion of a dialkyl methylphosphonate. Thus, 2-methyl-2-phenoxypropionyl chloride and dimethyl methylphosphonate yield dimethyl 2-oxo-3-methyl-3-phenoxybutylphosphonate. The acyl halides are readily available from the aliphatic acids by methods known in the art, e.g. chlorides are conveniently prepared using thionyl chloride.

Continuing with Chart B, the formula-XXX compound is obtained as a mixture of alpha and beta isomers by reduction of XXIX. For this reduction, use is made of any of the known ketonic carbonyl reducing agents which do not reduce ester or acid groups or carbon-carbon double bonds when the latter is undesirable. Examples of those are the metal borohydrides, especially sodium, potassium, and zinc borohydrides, lithium (tri-tert-butoxy)aluminum hydride, metal trialkoxy borohydrides, e.g., sodium trimethoxyborohydride, lithium borohydride, diisobutyl aluminum hydride, and when carbon-carbon double bond reduction is not a problem, the boranes, e.g., disiamylborane.

For production of natural-configuration PG-type compounds, the desired 15-alpha form of the formula-XXX compound is separated from the 15-beta isomer by silica gel chromatography.

The formula-XXXI compound is then obtained by deacylation of XXX with an alkali metal carbonate, for example potassium carbonate in methanol at about 25° C.

The bis(tetrahydropyranyl) ether XXXII is obtained by reaction of the formula-XXXI diol with dihydropyran in an inert solvent, e.g. dichloromethane, in the presence of an acid condensing agent such as p-toluenesulfonic acid or pyridine hydrochloride. The dihydropyran is used in excess, preferably 4 to 10 times theory. The reaction is normally complete in 15–30 min. at 20°–30° C.

The lactol XXXIII is obtained on reduction of the formula-XXXII lactone or its 15β epimer without reducing the 13,14-ethylenic group. For this purpose, diisobutylaluminum hydride is used. The reduction is preferably done at −60° to −70° C. The 15β-epimer of the formula-XXXII lactone is readily obtained by the steps of Chart B, using the 15β isomer of formula XXX.

The formula-XXXIV compound is obtained from the formula-XXXIII lactol by the Wittig reaction, using a Wittig reagent derived from the appropriate ω-carboxyalkyltriphenylphosphonium bromide, HOOC-$(CH_2)_{g+1}$-$P(C_6H_5)_3Br$, and sodio dimethylsulfinylcarbanide. The reaction is conveniently carried out at about 25° C. This formula-XXXIV compound serves as an intermediate for preparing either the $PGF_{2\alpha}$-type or the $PGE_2$-type product (Chart C). The phosphonium compounds are known in the art or are readily available, e.g. by reaction of an ω-bromoaliphatic acid with triphenylphosphine.

The formula-XXXV $PGF_{2\alpha}$-type product is obtained on hydrolysis of the tetrahydropyranyl groups from the formula-XXXIV compound, e.g. with methanol-HCl or with acetic acid/water/tetrahydrofuran at 40°–55° C.

Reference to Chart C will make clear the preparation of the $PGE_2$-type products. The formula-XXXVI bis(-tetrahydropyranyl) ether of the $PGF_{2\alpha}$-type products, either as an acid represented by formula XXIV or as an ester is oxidized at the 9-hydroxy position, preferably with Jones reagent. Finally the tetrahydropyranyl groups are replaced with hydrogen, by hydrolysis as in preparing the $PGF_{2\alpha}$-type product of Chart B. In Chart C, the symbols g, M, M', Q, and THP have the same meanings as in Charts A and B; $R_1$ is hydrogen or alkyl of one to 12 carbon atoms, inclusive,

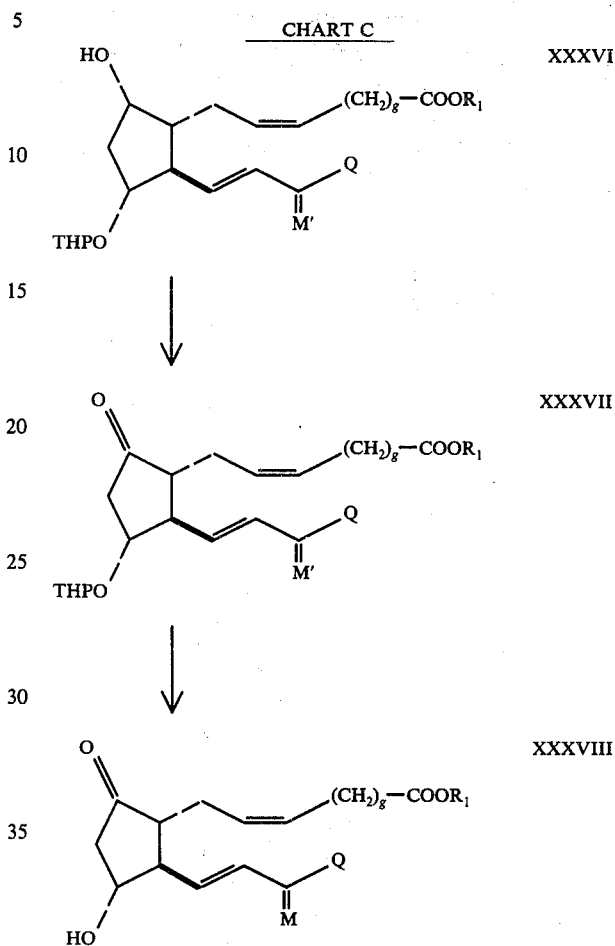

cycloalkyl of 3 to 10 carbon atoms, inclusive, aralkyl of 7 to 12 carbon atoms, inclusive, phenyl, or phenyl sub-substituted with one, 2, or 3 chloro or alkyl of one to 4 carbon atoms, inclusive. The esters, wherein $R_1$ is not hydrogen, are readily obtained by methods known in the art, e.g. reaction with diazoalkanes.

The formula-VIII $PGE_1$ and formula-XVIII 13,14-dihydro-$PGE_1$ type products of this invention are prepared by ethylenic reduction of the formula-XIII $PGE_2$ type compounds. Reducing agents useful for this transformation are known in the art. Thus, hydrogen is used at atmospheric pressure or low pressure with catalysts such as palladium on charcoal or rhodium on aluminum. See, for example, E. J. Corey et al., J. Am. Chem. Soc. 91, 5677 (1969) and B. Samuelsson, J. Biol. Chem. 239, 4091 (1964). For the $PGE_1$ type compounds, the reduction is terminated when one equivalent of hydrogen is absorbed; for the 13,14-dihydro-$PGE_1$ type compounds, when two equivalents are absorbed. The 13,14-dihydro-$PGE_1$ compounds are also obtained by reduction of the $PGE_1$ compounds. For preparing the $PGE_1$-type compounds it is preferred that a catalyst such as nickel boride be used which selectively effects reduction of the cis-5,6-carbon-carbon double bond in the presence of the trans-13,14 unsaturation. Mixtures of the products are conveniently separated by silica gel chromatography.

Alternatively, the bis(tetrahydropyranyl) ethers of the PGE₂ type compounds (Formula XXXVI) are reduced and subsequently hydrolyzed to remove the tetrahydropyranyl groups.

Chart D shows transformations from the formula-XXXIX PGE-type compounds to the corresponding PGF-, PGA-, and PGB-type compounds. In FIGS. XXXIX, XL, XLI, and XLII of Chart D, g, M, R₂, R₃, T, s, and ~ have the same meanings as in Charts A and B; R₁ has the same meanings as in Chart C; and (a) X is trans-CH=CH— or -CH₂CH₂-, and Y is -CH₂CH₂-, or (b) X is trans-CH=CH— and Y is cis-CH=CH—. When X is trans-CH=CH- and Y is -CH₂CH₂-, formula XXXIX represents PGE₁-type compounds; when X is —CH₂CH₂— and Y is —CH₂CH₂—, formula XXXIX represents 13,14-dihydro-PGE₁ type compounds; and when X is trans-CH=CH- and Y is cis-CH=CH—, formula XXXIX represents PGE₂-type compounds. Thus, formulas XXXIX, XL, XLI, and XLII embrace all of the compounds represented herein by formulas VIII-XXIII.

CHART D

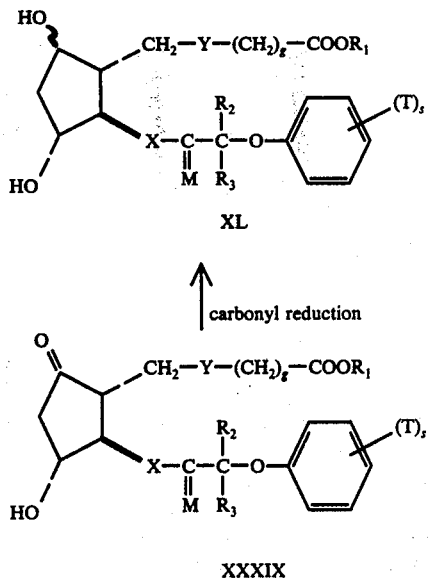

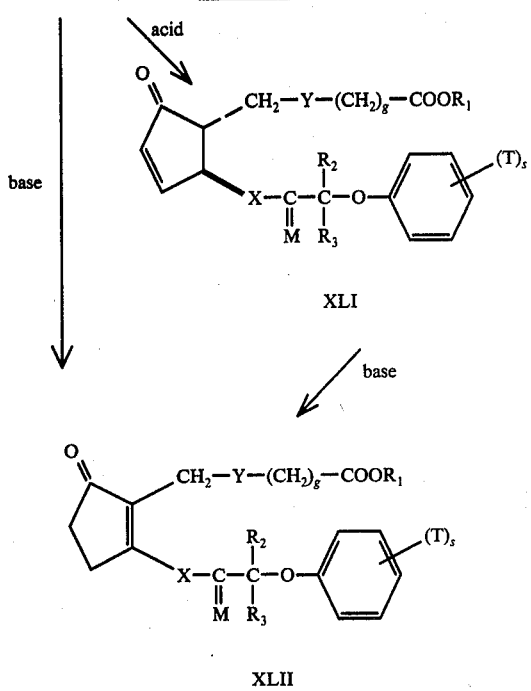

Thus, the various PGF$_\beta$-type compounds encompassed by formulas X, XV, and XX are prepared by carbonyl reduction of the corresponding PGE-type compounds of formulas VIII, XIII, and XVIII, respectively. For example, carbonyl reduction of 16-phenoxy-18,19,20-trinor-PGE₁ gives a mixture of 16-phenoxy-18,19,20-trinor-PGF$_{1\alpha}$ and 16-phenoxy-18,19,20-trinor-PGF$_{1\beta}$. These ring carbonyl reductions are carried out by methods known in the art for ring carbonyl reductions of known prostanoic acid derivatives. See, for example, Bergstrom et al., Arkiv Kemi 19, 563 (1963), Acta. Chem. Scand. 16, 969 (1962), and British specification No. 1,097,533. Any reducing agent is used which does not react with carbon-carbon double bonds or ester groups. Preferred reagents are lithium(tri-tert-butoxy)aluminum hydride, the metal borohydrides, especially sodium, potassium and zinc borohydrides, the metal trialkoxy borohydrides, e.g., sodium trimethoxyborohydride. The mixtures of alpha and beta hydroxy reduction products are separated into the individual alpha and beta isomers by methods known in the art for the separation of analogous pairs of known isomeric prostanoic acid derivatives. See, for example, Bergstrom et al., cited above, Granstrom et al., J. Biol. Chem. 240, 457 (1965), and Green et al., J. Lipid Research 5, 117 (1964). Especially preferred as separation methods are partition chromatographic procedures, both normal and reversed phase, preparative thin layer chromatography, and countercurrent distribution procedures.

The various PGA-type compounds encompassed by formulas XI, XVI, and XXI are prepared by acidic dehydration of the corresponding PGE-type compounds of formulas VIII, XIII, and XVIII. For example, acidic dehydration of 16-methyl-16-phenoxy-18,19,20-trinor-PGE₂ gives 16-methyl-16-phenoxy-18,19,20-trinor-PGA₂.

These acidic dehydrations are carried out by methods known in the art for acidic dehydrations of known prostanoic acid derivatives. See, for example, Pike et al., Proc. Nobel Symposium II, Stockholm (1966), Interscience Publishers, New York, pp. 162–163 (1967); and British specification 1,097,533. Alkanoic acids of 2 to 6 carbon atoms, inclusive, especially acetic acid, are preferred acids for this acidic dehydration. Dilute aqueous solutions of mineral acids, e.g., hydrochloric acid, especially in the presence of a solubilizing diluent, e.g., tetrahydrofuran, are also useful as reagents for this acidic dehydration, although these reagents may cause partial hydrolysis of an ester reactant.

The various PGB-type compounds encompassed by formulas XII, XVII, and XXII are prepared by basic dehydration of the corresponding PGE-type compounds encompassed by formulas VIII, XIII, and XVIII, respectively, or by contacting the corresponding PGA-type compounds encompassed by formulas XI, XVI, and XXI, respectively, with base. For example, both 16-(p-chlorophenoxy)-18,19,20-trinor-13,14-dihydro-PGE$_1$ and 16-(p-chlorophenoxy)-18,19,20-trinor-13,14-dihydro-PGA$_1$ give 16-(p-chlorophenoxy)-18,19,20-trinor-13,14-dihydro-PGB$_1$ on treatment with base.

These basic dehydrations and double bond migrations are carried out by methods known in the art for similar reactions of known prostanoic acid derivatives. See, for example, Bergstrom et al., J. Biol. Chem. 238, 3555 (1963). The base is any whose aqueous solution has pH greater than 10. Preferred bases are the alkali metal hydroxides. A mixture of water and sufficient of a water-miscible alkanol to give a homogeneous reaction mixture is suitable as a reaction medium. The PGE-type or PGA-type compound is maintained in such a reaction medium until no further PGB-type compound is formed, as shown by the characteristic ultraviolet light absorption near 278 m$\mu$ for the PGB-type compound.

Optically active compounds are obtained from optically active intermediates according to the process steps of Charts A and B. Likewise, optically active products are obtained by the transformations of optically active compounds following the processes of Charts C and D. When racemic intermediates are used in reactions corresponding to the processes of Charts A-D, inclusive, and racemic products are obtained, these racemic products may be used in their racemic form or, if preferred, they may be resolved as optically active isomers by procedures known in the art.

For example, when final compound VIII to XXIII is a free acid, the dl form thereof is resolved into the $d$ and $l$ forms by reacting said free acid by known general procedures with an optically active base, e.g., brucine or strychnine, to give a mixture of two diastereoisomers which are separated by known general procedures, e.g., fractional crystallization, to give the separate diastereoisomeric salts. The optically active acid of formula VIII to XXIII is then obtained by treatment of the salt with an acid by known general procedures.

As discussed above, the stereochemistry at C-15 is not altered by the transformations of Charts A and B; the 15$\beta$ epimeric products of formula XXXV are obtained from 15$\beta$ formula-XXX reactants. Another method of preparing the 15$\beta$ products is by isomerization of the PGF$_1$- or PGE$_1$-type compounds having 15$\alpha$ configuration, by methods known in the art. See, for example, Pike et al., J. Org. Chem. 34, 3552 (1969).

As discussed above, the processes of Charts B, C, and D lead variously to acids (R$_1$ is hydrogen) or to esters (R$_1$ is alkyl, cycloalkyl, aralkyl, phenyl or substituted phenyl, as defined above). When an acid has been prepared and an alkyl ester is desired, esterification is advantageously accomplished by interaction of the acid with the appropriate diazohydrocarbon. For example, when diazomethane is used, the methyl esters are produced. Similar use of diazoethane, diazobutane, and 1-diazo-2-ethylhexane, and diazodecane, for example, gives the ethyl, butyl, and 2-ethylhexyl and decyl esters, respectively.

Esterification with diazohydrocarbons is carried out by mixing a solution of the diazohydrocarbon in a suitable inert solvent, preferably diethyl ether, with the acid reactant, advantageously in the same or a different inert diluent. After the esterification reaction is complete, the solvent is removed by evaporation, and the ester purified if desired by conventional methods, preferably by chromatography. It is preferred that contact of the acid reactants with the diazohydrocarbon be no longer than necessary to effect the desired esterification, preferably about one to about ten minutes, to avoid undesired molecular changes. Diazohydrocarbons are known in the art or can be prepared by methods known in the art. See, for example, Organic Reactions, John Wiley and Sons, Inc., New York, N.Y., Vol. 8, pp. 389–394 (1954).

An alternative method for esterification of the carboxyl moiety of the acid compounds comprises transformation of the free acid to the corresponding silver salt, followed by interaction of that salt with an alkyl iodide. Examples of suitable iodides are methyl iodide, ethyl iodide, butyl iodide, isobutyl iodide, tert-butyl iodide, and the like. The silver salts are prepared by conventional methods, for example, by dissolving the acid in cold dilute aqueous ammonia, evaporating the excess ammonia at reduced pressure, and then adding the stoichiometric amount of silver nitrate.

The final formula VII-to-XXIII compounds prepared by the processes of this invention, in free acid form, are transformed to pharmacologically acceptable salts by neutralization with appropriate amounts of the corresponding inorganic or organic base, examples of which correspond to the cations and amines listed above. These transformations are carried out by a variety of procedures known in the art to be generally useful for the preparation of inorganic, i.e., metal or ammonium, salts, amine acid addition salts, and quaternary ammonium salts. The choice of procedure depends in part upon the solubility characteristics of the particular salt to be prepared. In the case of the inorganic salts, it is usually suitable to dissolve the formula VIII-to-XXIII acid in water containing the stoichiometric amount of a hydroxide, carbonate, or bicarbonate corresponding to the inorganic salt desired. For example, such use of sodium hydroxide, sodium carbonate, or sodium bicarbonate gives a solution of the sodium salt. Evaporation of the water or addition of a water-miscible solvent of moderate polarity, for example, a lower alkanol or a lower alkanone, gives the solid inorganic salt if that form is desired.

To produce an amine salt, the formula VIII-to-XXIII acid is dissolved in a suitable solvent of either moderate or low polarity. Examples of the former are ethanol, acetone, and ethyl acetate. Examples of the latter are diethyl ether and benzene. At least a stoichiometric amount of the amine corresponding to the desired cation is then added to that solution. If the resulting salt does not precipitate, it is usually obtained in solid form by addition of a miscible diluent of low polarity or by evaporation. If the amine is relatively volatile, any excess can easily be removed by evaporation. It is preferred to use stoichiometric amounts of the less volatile amines.

Salts wherein the cation is quaternary ammonium are produced by mixing the formula VIII-to-XXIII acid with the stoichiometric amount of the corresponding quaternary ammonium hydroxide in water solution, followed by evaporation of the water.

The final formula VIII-to-XXIII acids or esters prepared by the processes of this invention are transformed to lower alkanoates by interaction of the formula VIII-to-XXIII hydroxy compound with a carboxyacylating agent, preferably the anhydride of a lower alkanoic acid, i.e., an alkanoic acid of two to 8 carbon atoms, inclusive. For example, use of acetic anhydride gives the corresponding acetate. Similar use of propionic anhydride, isobutyric anhydride, and hexanoic acid anhydride gives the corresponding carboxyacylates.

The carboxyacylation is advantageously carried out by mixing the hydroxy compound and the acid anhydride, preferably in the presence of a tertiary amine such as pyridine or triethylamine. A substantial excess of the anhydride is used, preferably about 10 to about 10,000 moles of anhydride per mole of the hydroxy compound reactant. The excess anhydride serves as a reaction diluent and solvent. An inert organic diluent, for example, dioxane, can also be added. It is preferred to use enough of the tertiary amine to neutralize the carboxylic acid produced by the reaction, as well as any free carboxyl groups present in the hydroxy compound reactant.

The carboxyacylation reaction is preferably carried out in the range about 0° to about 100° C. The necessary reaction time will depend on such factors as the reaction temperature, and the nature of the anhydride and tertiary amine reactants. With acetic anhydride, pyridine, and a 25° C. reaction temperature, a 12 to 24-hour reaction time is used.

The carboxyacylated product is isolated from the reaction mixture by conventional methods. For example, the excess anhydride is decomposed with water, and the resulting mixture acidified and then extracted with a solvent such as diethyl ether. The desired carboxyacylate is recovered from the diethyl ether extract by evaporation. The carboxyacylate is then purified by conventional methods, advantageously by chromatography.

By this procedure, the formula VIII, XIII, and XVIII PGE-type compounds are transformed to dialkanoates, the formula IX, X, XIV, XV, XIX, and XX PGF-type compounds are transformed to trialkanoates, and the formula XI, XVI, and XXI PGA-type and formula XII, XVII, and XXII PGB-type compounds are transformed to monoalkanoates.

When a PGE-type dialkanoate is transformed to a PGF-type compound by carbonyl reduction as shown in Chart D, a PGF-type dialkanoate is formed and is used for the above-described purposes as such or is transformed to a trialkanoate by the above-described procedure. In the latter case, the third alkanoyloxy group can be the same as or different from the two alkanoyloxy groups present before the carbonyl reduction.

DESCRIPTION OF THE PREFERRED EMBODIMENTS

The invention can be more fully understood by the following preparation and examples.

All temperatures are in degrees centigrade.

Infrared absorption spectra are recorded on a Perkin-Elmer model 421 infrared spectrophotometer. Except when specified otherwise, undiluted (neat) samples are used.

Mass spectra are recorded on an Atlas CH-4 mass spectrometer with a TO-4 source (ionization voltage 70 ev).

NMR spectra are recorded on a Varian A-60 spectrophotometer using solutions in deuterochloroform or other appropriate solvents with tetramethylsilane as an internal standard (downfield).

"Brine", herein, refers to an aqueous saturated sodium chloride solution.

Preparation 1

3α-Benzoyloxy-2β-carboxaldehyde-5α-hydroxy-1α-cyclopentaneacetic Acid γ-Lactone (Formula XXVIII: $R_5$ is benzoyl)

Refer to Chart A. a. To a mixture of formula-XXIV laevorotatory (−) 3α-hydroxy-5α-hydroxy-4-iodo-2β-methoxymethyl-1α-cyclopentaneacetic acid γ-lactone (E. J. Corey et al., J. Am. Chem. Soc. 92, 297 (1970), 75 g.) in 135 ml. of dry pyridine under a nitrogen atmosphere is added 30.4 ml. of benzoyl chloride with cooling to maintain the temperature at about 20°-40° C. Stirring is continued for an additional 30 min. About 250 ml. of toluene is added and the mixture concentrated under reduced pressure. The residue is dissolved in one liter of ethyl acetate, washed with 10% sulfuric acid, brine, aqueous saturated sodium bicarbonate, and brine. The ethyl acetate solution is dried over sodium sulfate and concentrated under reduced pressure to yield an oil, 95 g. Crystallization of the oil yields the corresponding 3α-benzoyloxy compound, m.p. 84°-86° C.; $[α]_D$ +7° (CHCl₃); infrared spectral absorptions at 1768, 1722, 1600, 1570, 1490, 1275, 1265, 1180, 1125, 1090, 1060, 1030, and 710 cm$^{-1}$; and NMR (nuclear magnetic resonance) peaks at 2.1-3.45, 3.3, 3.58, 4.38, 5.12, 5.51, 7.18-7.58, and 7.83-8.05 δ.

b. The iodo group is removed as follows. To a solution of the above benzoyloxy compound (60 g.) in 240 ml. of dry benzene is added 2,2'-azobis-(2-methylpropionitrile) (approximately 60 mg.). The mixture is cooled to 15° C. and to it is added a solution of 75 g. tributyltin hydride in 600 ml. of ether, with stirring, at such a rate as to maintain continuous reaction at about 25° C. When the reaction is complete as shown by TLC (thin layer chromatography) the mixture is concentrated under reduced pressure to an oil. The oil is mixed with 600 ml. of Skellysolve B (mixed isomeric hexanes) and 600 ml. of water and stirred for 30 min. The water layer, containing the product, is separated, then combined with 450 ml. of ethyl acetate and enough solid sodium chloride to saturate the aqueous phase. The ethyl acetate layer, now containing the product, is separated, dried over magnesium sulfate, and concentrated under reduced pressure to an oil, 39 g. of the iodine-free compound. An analytical sample gives $[α]_D$ −99° (CHCl₃); infrared spectral absorptions at 1775, 1715, 1600, 1585, 1490, 1315, 1275, 1180, 1110, 1070, 1055, 1025, and 715 cm$^{-1}$.; NMR peaks at 2.5-3.0, 3.25, 3.34, 4.84–5.17, 5.17–5.4, 7.1–7.5, and 7.8–8.05 δ; and mass spectral peaks at 290, 168, 105, and 77.

c. The 2β-methoxymethyl compound is changed to a hydroxymethyl compound as follows. To a cold (0.5° C.) solution of the above iodine-free methoxy-methyl lactone (20 g.) in 320 ml. of dichloromethane under nitrogen is added a solution of 24.8 ml. of boron tribromide in 320 ml. of dichloromethane, dropwise with vigorous stirring over a period of 50 min. at 0°–5° C. Stirring and cooling are continued for one hr. When the reaction is complete, as shown by TLC, there is cautiously added a solution of sodium carbonate (78 g.) monohydrate in 200 ml. of water. The mixture is stirred at 0°–5° C. for 10–15 min., saturated with sodium chloride, and the ethyl acetate layer separated. Additional ethyl acetate extractions of the water layer are combined with the main ethyl acetate solution. The combined solutions are rinsed with brine, dried over sodium sulfate and concentrated under reduced pressure to an oil, 18.1 g. of the 2β-hydroxymethyl compound. An analytical sample has m.p. 116°–118° C.; $[\alpha]_D$ −80° (CHC$_{l3}$); infrared spectral absorptions at 3460, 1735, 1708, 1600, 1580, 1490, 1325, 1315, 1280, 1205, 1115, 1090, 1070, 1035, 1025, 730, and 720; and NMR peaks at 2.1–3.0, 3.58, 4.83–5.12, 5.2–5.45, 7.15–7.55, and 7.8–8.0 δ.

d. The title 2β-carboxaldehyde compound is prepared as follows. To a mixture of 250 ml. of dichloromethane and Collins' reagent prepared from chromium trioxide (10.5 g.) and 16.5 ml. of pyridine, cooled to 0° C., a cold solution of the hydroxymethyl compound of step c (5.0 g.) in 50 ml. of dichloromethane is added, with stirring. After 7 min. of additional stirring, the title intermediate is used directly without isolation (see Example 1).

Following the procedure of Preparation 1, but replacing that optically active formula-XXIV iodolactone with the racemic compound of that formula and the mirror image thereof (see E. J. Corey et al., J. Am. Chem. Soc. 91, 5675 (1969)) there is obtained the racemic compound corresponding to formula XXVIII.

EXAMPLE 1

3α-Benzoyloxy-5α-hydroxy-2β-(3-oxo-4-phenoxytrans-1-butenyl)-1α-cyclopentaneacetic Acid, γ-Lactone (Formula XXIX: R$_2$ and R$_3$ are hydrogen, R$_5$ is benzoyl, and s is zero)

Refer to Chart B. a. There is first prepared dimethyl 3-phenoxyacetonylphosphonate. A solution of dimethyl methylphosphonate (75 g.) in 700 ml. of tetrahydrofuran is cooled to −75° C. under nitrogen and n-butyllithium (400 ml. of 1.6 molar solution in hexane) is added, keeping the temperature below −55° C. The mixture is stirred for 10 min. and to it is slowly added phenoxyacetyl chloride (44 g.), again keeping the temperature below −55° C. The reaction mixture is stirred at −75° C. for 2 hrs., then at about 25° C. for 16 hrs. The mixture is acidified with acetic acid and concentrated under reduced pressure. The residue is partitioned between diethyl ether and water, and the organic phase is dried and concentrated to the above-named intermediate, 82 g. Further treatment by silica gel chromatography yields an analytical sample having NMR peaks at 7.4–6.7 (multiplet), 4.78 (singlet), 4.8 and 4.6 (two singlets), and 3.4–3.04 (doublet) δ.

b. The phosphonate anion (ylid) is then prepared as follows. Dimethyl 3-phenoxyacetonylphosphonate (step a, 9.3 g.) is added in portions to a cold (5° C.) mixture of sodium hydride (1.75 g.), 50% in 250 ml. of tetrahydrofuran, and the resulting mixture is stirred for 1.5 hrs. at about 25° C.

c. To the mixture of step b is added the cold solution of the formula-XXVIII 2β-carboxaldehyde of Preparation 1, and the resulting mixture is stirred about 1.6 hrs. Then 3 ml. of acetic acid is added and the mixture is concentrated under reduced pressure. A solution is prepared from the residue in 500 ml. of ethyl acetate, washed with several portions of water and brine, and concentrated under reduced pressure. The residue is subjected to silica gel chromatography, eluting with ethyl acetate-Skellysolve B (isomeric hexanes) (3:1). Those fractions shown by TLC to be free of starting material and impurities are combined and concentrated to yield the title compound, 1.7 g.; NMR peaks at 5.0–8.2 and 4.7 (singlet) δ.

Following the procedure of Example 1, but replacing the optically active formula-XXVIII aldehyde with the racemic aldehyde obtained after Preparation 1, there is obtained the racemic 3-oxo-4-phenoxy-1-butenyl compound corresponding to formula XXIX.

Following the procedure of Example 1, but replacing phenoxyacetyl chloride with each of the following aliphatic acid esters there is obtained the corresponding phosphonate and thence the formula-XXIX lactone wherein R$_5$ is benzoyl:

methyl 2-phenoxypropionate
methyl 2-methyl-2-phenoxypropionate
ethyl 2-phenoxybutyrate
methyl 2-ethyl-2-phenoxybutyrate
ethyl 2-methyl-2-phenoxybutyrate
methyl 2-(p-tolyloxy)acetate
methyl 2-(p-fluorophenoxy)propionate
ethyl 2-(o,p-dichlorophenoxy)-2-methyl-propionate
ethyl 2-(α,α,α-trifluoro-p-tolyloxy)butyrate and
methyl 2-(m-methoxyphenoxy)-2-methyl-butyrate.

For example, methyl 2-phenoxypropionate yields dimethyl 2-oxo-3-phenoxybutylphosphonate and, thence, the formula-XXIX 3α-benzoyloxy-5α-hydroxy-2β-(3-oxo-4-phenoxy-trans-1-pentenyl)-1α-cyclopentaneacetic acid γ-lactone. Likewise, ethyl 2-(o,p-dichlorophenoxy)-2-methyl-propionate yields dimethyl 2-oxo-3-(o,p-dichlorophenoxy)-3-methylbutylphosphonate and, thence, the formula-XXIX 3α-benzoyloxy-5α-hydroxy-2β-[3-oxo-4-(o,p-dichlorophenoxy)-4-methyl-trans-1-pentenyl]-1α-cyclopentaneacetic acid γ-lactone.

When the phosphonate contains an asymmetric carbon atom, e.g. when the methylene between the carbonyl and the —O— is substituted with only one methyl or ethyl group, the phosphonate exists in either of two optically active forms (+ or −) or their racemic (dl) mixture. An optically active phosphonate is obtained by starting with an appropriate optically active isomer of a phenoxy of substituted-phenoxy aliphatic acid. Methods of resolving these acids are known in the art, for example by forming salts with an optically active base such as brucine, separating the resulting diastereomers, and recovering the acids.

Following the procedure of Example 1, employing the optically active aldehyde XXVIII of that example, each optically active phosphonate obtained from the list of aliphatic acid esters above in the second paragraph following Example 1 yields a corresponding optically active formula-XXIX γ-lactone.

Likewise following the procedure of Example 1, employing the optically active aldehyde XXVIII of that example, each racemic phosphonate obtained from the above-mentioned list of aliphatic acid esters yields a pair of diastereomers, differing in their stereochemistry at the fourth carbon of the phenoxy-terminated side-chain. These diastereomers are separated by conventional methods, e.g. by silica gel chromatography.

Again following the procedure of Example 1, employing the optically active aldehyde XXVIII of that example, each of the optically inactive phosphonates obtained from the list of aliphatic acid esters above wherein there is no asymmetric carbon atom, i.e. $R_2$ and $R_3$ are the same, yields a corresponding optically active formula-XXIX γ-lactone.

Replacing the optically active aldehyde XXVIII with the racemic aldehyde obtained after Preparation 1, and following the procedure of Example 1 using each of the optically active phosphonates described above, there is obtained in each case a pair of diastereomers which are separated by chromatography.

Likewise following the procedure of Example 1, employing the racemic aldehyde with each of the racemic phosphonates described above, there are obtained in each case two pairs of 3-oxo-4-phenoxy (or substituted-phenoxy) racemates which are separated into pairs of racemic compounds by methods known in the art, e.g. silica gel chromatography.

Again following the procedure of Example 1, employing the racemic aldehyde with each of the optically inactive phosphonates described above, there are obtained in each case a racemic product corresponding to formula XXIX.

EXAMPLE 2

3α-Benzoyloxy-5α-hydroxy-2β-(3α-hydroxy-4-phenoxy-trans-1-butenyl)-1α-cyclpentaneacetic Acid, γ-Lactone (Formula XXX: M is

Q is

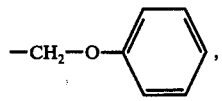

and $R_5$ is benzoyl); and the 3β-hydroxy isomer (Formula XXX: M is

).

Refer to Chart B. Sodium borohydride (1.05 g.) is added in portions to a cold (0° C.) mixture of zinc chloride (4.4 g.) and 35 ml. of 1,2-dimethoxyethane under nitrogen. Stirring is continued at about 25° C. for 20 hrs. Then the mixture is cooled to −20° C. and the formula-XXIX 3-oxo compound (Example 1, 2.6 g. in 10 ml. of 1,2-dimethoxyethane) is added. The mixture is stirred at −20° C. for 6 hrs., and at 25° C. for 30 min. The mixture is again cooled to −20° C. and 5 ml. of water is added dropwise. The mixture is shaken with 100 ml. of brine and ethyl acetate and the organic layer is dried and concentrated under reduced pressure. The residue is chromatographed on silica gel, eluting with ethyl acetate-Skellysolve B (isomeric hexanes) (3:1). Those fractions shown by TLC to be free of starting material and impurities are combined and concentrated to yield the 3α-hydroxy title compound, 1.1 g.; NMR peaks at 6.6–8.0, 5.52–5.87, and 3.83 δ. Other fractions yield the more polar 3β-hydroxy title compound, 0.8 g.; NMR peaks at 6.6–8.0, 5.52–5.87, and 3.83 δ.

Following the procedure of Example 2, but using the racemic 3-oxo-4-phenoxy-1-butenyl compound obtained following Example 1, there are obtained the corresponding racemic 3-hydroxy products.

Likewise following the procedure of Example 2, each of the optically active or racemic lactones corresponding to formula XXIX described following Example 1 is transformed to the optically active or racemic compound corresponding to formula XXX.

EXAMPLE 3

3α,5α-Dihydroxy-2β-(3α-hydroxy-4-phenoxytrans-1-butenyl)-1α-cyclopentaneacetaldehyde γ-Lactol Bis(tetrahydropyranyl) Ether (Formula XXXIII: M' is

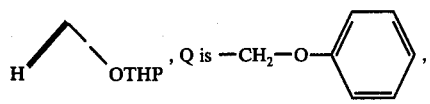

and ~ is alpha or beta).

Refer to Chart B. a. The formula-XXX 3α-hydroxy compound (Example 2, 1.35 g.) in 22 ml. of anhydrous methanol is stirred with potassium carbonate (0.48 g.) for 1 hr. at about 25° C. Then 15 ml. of chloroform is added and the solvent removed under reduced pressure. A solution of the residue in 70 ml. of chloroform is shaken with 10 ml. of water containing potassium hydrogen sulfate (0.5 g.), then with brine, and concentrated. The residue is washed with several portions of Skellysolve B (isomeric hexanes) and dried to yield the formula-XXXI benzoyloxy-free compound, i.e. 3α,5α-dihydroxy-2β-(3α-hydroxy-4-phenoxy-trans-1-butenyl)-1α-cyclopentaneacetic acid, γ-lactone, 0.4 g.

b. The formula-XXXI compound from part a above is converted to the formula-XXXII bis(tetrahydropyranyl) ether by reaction with 0.8 ml. of dihydropyran in 10 ml. of dichloromethane in the presence of pyridine hydrochloride (about 0.03 g.). In about 2.5 hrs. the mixture is filtered and concentrated to the formula-XXXII product, 0.6 g.; having no infrared absorption at 3300 cm$^{-1}$.

c. The title compound is prepared as follows. Diisobutylaluminum hydride (4.8 ml. of a 10% solution in toluene) is added dropwise to a stirred solution of the formula-XXXII bis(tetrahydropyranyl) ether from part b above in 8 ml. of toluene cooled to −78° C. Stirring is continued at −78° C. for 0.5 hr., whereupon a solution of 3 ml. of tetrahydrofuran and 1 ml. of water is added cautiously. After the mixture warms to 25° C. it is filtered and the filtrate washed with brine, dried, and concentrated to the mixed alpha and beta hydroxy isomers of the formula-XXXIII title compounds, 0.33 g., having infrared absorption at 3300 cm$^{-1}$.

Following the procedures of Example 3, but using the formula-XXX 3β-hydroxy-4-phenoxy isomer of Example 2, there is obtained the corresponding 3β-hydroxy formula-XXXIII compound, i.e. wherein M' is

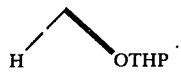

Likewise following the procedures of Example 3, each of the optically active or racemic compounds corresponding to formula XXX described following Example 2 is transformed to an optically active or racemic compound corresponding to formula XXXIII. There are thus obtained both the 3α- and 3β-hydroxy isomers.

EXAMPLE 4

16-Phenoxy-17,18,19,20-tetranor-PGF$_{2\alpha}$, 11, 15-Bis(tetrahydropyranyl) Ether (Formula XXXIV: g is 3, M' is

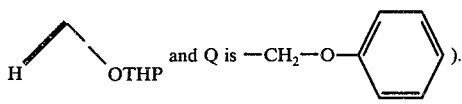

Refer to Chart B. 4-Carboxybutyltriphenylphosphonium bromide (E. J. Corey et al., J. Am. Chem. Soc. 91, 5677 (1969)) (0.9 g.) is added to a solution of sodio dimethylsulfinylcarbanide prepared from sodium hydride (0.195 g.) and 5 ml. of dimethylsulfoxide (DMSO). To this Wittig reagent is added dropwise a solution of the formula-XXXIII lactol (Example 3, 0.33 g.) in 2 ml. of DMSO. The mixture is stirred at about 25° C. for 2 hrs., then diluted with 20 ml. of benzene. To the mixture is added, with stirring, a solution of potassium hydrogen sulfate (0.7 g.) in 5 ml. of water. The organic layer is separated, washed with water and brine, then dried and concentrated to an oil, 1.7 g. This residue is subjected to silica gel chromatography, eluting with 0-20% acetone in dichloromethane. Those fractions shown by TLC to contain the product free of starting material and impurities are combined and concentrated to yield the title compound, 0.3 g.; NMR peaks at 6.7-7.3, 5.2-5.75, 4.6, and 3.68 δ.

EXAMPLE 5

16-Phenoxy-17,18,19,20-tetranor-PGF$_{2\alpha}$ (Formula XIV: g is 3; M is

R$_1$, R$_2$, and R$_3$ are hydrogen; and s is zero).

Refer to Chart B. A solution of the formula-XXXIV bis(tetrahydropyranyl) ether (Example 4, 0.3 g.) in 5 ml. of methanol, 0.2 ml. of hydrochloric acid, and 2 ml. of water is stirred at about 25° C for 1.5 hrs. The solution is made basic to pH 8-9 with dilute sodium hydroxide and extracted with dichloromethane. The aqueous phase is then acidified to pH 2 with dilute hydrochloric acid and extracted with ethyl acetate. The organic phase is dried and concentrated under reduced pressure to an oil. The oil is chromatographed on silica gel, eluting with 0-10% methanol in ethyl acetate. Those fractions shown by TLC to contain the product free of starting material and impurities are combined and concentrated to yield the title compound, 0.06 g.; mass spectral peaks (trimethylsilyl derivative) at 678, 663, 578, 561, 481, and 391; NMR peaks at 6.7-7.3, 5.5-5.7, and 5.0-5.4 δ.

Following the procedures of Examples 4 and 5, each of the optically active or racemic 3α-hydroxy compounds corresponding to formula XXXIII described following Example 3 is transformed to the corresponding bis(tetrahydropyranyl) ether and thence to the corresponding 16-phenoxy (or substituted-phenoxy)-PGF$_{1\alpha}$ type compound or racemic mixture. There are thus obtained the following compounds from the 3α-hydroxy isomers:

16-phenoxy-17,18,19,20-tetranor-PGF$_{2\alpha}$
16-phenoxy-18,19,20-trinor-PGF$_{2\alpha}$
16-methyl-16-phenoxy-18,19,20-trinor-PGF$_{2\alpha}$
16-phenoxy-19,20-dinor PGF$_{2\alpha}$
16-ethyl-16-phenoxy-19,20-dinor-PGF$_{2\alpha}$
16-methyl-16-phenoxy-19,20-dinor-PGF$_{2\alpha}$
16-(p-tolyloxy)-17,18,19,20-tetranor-PGF$_{2\alpha}$
16-(p-fluorophenoxy)-18,19,20-trinor-PGF$_{2\alpha}$
16-(o,p-dichlorophenoxy)-16-methyl-18,19,20-trinor-PGF$_{2\alpha}$
16-(α,α,α-trifluoro-p-tolyloxy)-19,20-dinor-PGF$_{2\alpha}$
16-methyl-16-(m-methoxyphenoxy)-19,20-dinor-PGF$_{2\alpha}$
and their racemic mixtures, for example dl-16-phenoxy-17,18,19,20-tetranor-PGF$_{2\alpha}$.

Likewise following the procedures of Examples 4 and 5 but employing the above-described 3β-hydroxy compounds corresponding to formula XXXIII, there are obtained the corresponding 15β-epimers and their racemic mixtures for example:

16-phenoxy-17,18,19,20-tetranor-15β-PGF$_{2\alpha}$
16-phenoxy-18,19,20-trinor-15β-PGF$_{2\alpha}$
16-methyl-16-phenoxy-18,19,20-trinor-15β-PGF$_{2\alpha}$ Following the procedures of Examples 4 and 5, but replacing 4-carboxybutyltriphenylphosphonium bromide with a phosphonium bromide within the scope of HOOC-(CH$_2$)$_{g+1}$-P(C$_6$H$_5$)$_3$Br wherein g is 2, 4, or 5, namely 3-carboxypropyltriphenylphosphonium bromide,
5-carboxypentyltriphenylphosphonium bromide, or
6-carboxyhexyltriphenylphosphonium bromide, each of the optically active or racemic 3α-hydroxy compounds corresponding to formula XXXIII described following Example 3 is transformed to a bis(tetrahydropyranyl) ether corresponding to formula XXXIV wherein the carboxy-terminated side chain has six, eight, or nine carbon atoms, and, thence, to the corresponding 16-phenoxy (or substituted-phenoxy)-PGF$_{2\alpha}$ type compound or racemic mixture, for example:

16-phenoxy-2,17,18,19,20-pentanor-PGF$_{2\alpha}$
16-phenoxy-2a-homo-18,19,20-trinor-PGF$_{2\alpha}$ 16-methyl-16-phenoxy-2a,2b-dihomo-19,20-dinor-PGF$_{2\alpha}$
16-phenoxy-2,19,20-trinor-PGF$_{2\alpha}$
16-ethyl-16-phenoxy-2a-homo-19,20-dinor-PGF$_{2\alpha}$
16-methyl-16-phenoxy-2a,2b-dihomo-19,20-dinor-PGF$_{2\alpha}$
16-(p-tolyloxy)-2,17,18,19,20-pentanor-PGF$_{2\alpha}$
16-(p-fluorophenoxy)-2a-homo-18,19,20-trinor-PGF$_{2\alpha}$
16-(o,p-dichlorophenoxy)-16-methyl-2a,2b-dihomo-18,19,20-trinor-PGF$_{2\alpha}$
16-($\alpha,\alpha,\alpha$-trifluoro-p-tolyloxy)-2,19,20-trinor-PGF$_{2\alpha}$
16-methyl-16-(m-methoxyphenoxy)-2a-homo-19,20-dinor-PGF$_{2\alpha}$ and their racemic mixtures, for example dl-16-phenoxy-2,17,18,19,20-pentanor-PGF$_{2\alpha}$.

Likewise following the procedures of Examples 4 and 5 but employing with the various phosphonium bromides the 3$\beta$-hydroxy compounds corresponding to formula XXXIII described following Example 3, there are obtained the corresponding 15$\alpha$ epimers first as the bis(tetrahydropyranyl) ethers and then as the PGF$_{2\alpha}$ type products and their racemic mixtures, for example 16-phenoxy-2,17,18,19,20-pentanor-15$\beta$-PGF$_{2\alpha}$ and dl-16-phenoxy-2,17,18,19,20-pentanor-15$\beta$-PGF$_{2\alpha}$.

EXAMPLE 6

16-Phenoxy-17,18,19,20-tetranor-PGE$_2$ Methyl Ester (Formula XIII: g is 3, M is

R$_1$ is methyl, R$_2$ and R$_3$ are hydrogen, and s is zero).

Refer to Chart C.

a. There is first prepared the methyl ester of the formula-XXXIV 11,15-bis(tetrahydropyranyl) ether of 16-phenoxy-17,18,19,20-tetranor PGF$_{2\alpha}$. A solution of that formula-XXXIV compound (Example 4, 1.35 g.) in 10 ml. of diethyl ether is mixed with a solution of diazomethane (about 0.5 g.) in 25 ml. of diethyl ether and stirred for about 3 min. Two ml. of acetic acid is added, then about 50 ml. of ether, and the solution shaken with aqueous sodium bicarbonate solution. The organic phase is concentrated under reduced pressure to an oil. The oil is chromatographed on silica gel, eluting with ethyl acetate-Skellysolve B (isomeric hexanes) (3:1). The methyl ester is obtained, 0.42 g., NMR peak at 3.57 (singlet) $\delta$, and infrared absorption at 1745 cm$^{-1}$.

b. A solution of the product of step a (0.42 g.) in 12 ml. of acetone is cooled to about $-20°$ C. and to it is added slowly 0.5 ml. of Jones reagent (2.1 g. of chromium trioxide, 6 ml. of water, and 1.7 ml. of concentrated sulfuric acid). The mixture is stirred for 15 min., and then shaken with 30 ml. of ice water and 200 ml. of dichloro-methane-diethyl ether (1:3). The organic phase is washed with cold dilute hydrochloric acid, cold water, and brine, then dried and concentrated. The residue is the bis(tetrahydropyranyl) ether of the title compound, an oil, 0.35 g., having infrared absorption at 1740 cm$^{-1}$.

c. A solution of the product of step b in 9.5 ml. of acetic acid and 4.5 ml. of water is stirred at 37°-39° C. for 2.5 hrs. The mixture is neutralized with sodium bicarbonate solution, then saturated with salt and shaken with dichloro-methane-diethyl ether (1:3), dried and concentrated. The residue is chromatographed on silica gel, eluting with 25% ethyl acetate in Skellysolve B (isomeric hexanes), and 0-6% methanol in ethyl acetate. The fractions shown by TLC to contain the desired product free of starting material and impurities are combined and concentrated to yield the title compund, 0.10 g.; NMR peaks at 7.5–6.6, 5.7, 5.3, and 3.6 (singlet) $\delta$; infrared absorption bands at 3300, 1740, and 1730 cm$^{-1}$; mass spectral peaks at (trimethylsilyl derivative) at 546, 531, 515, 439, and 349.

Example 7

16-Methyl-16-phenoxy-18,19,20-trinor-PGF$_{2\alpha}$ (Formula XIV: g is 3, M is

R$_1$ is hydrogen, R$_2$ and R$_3$ are methyl, s is zero, and ~ is alpha).

Refer to Chart B.

a. There is first prepared dimethyl 2-oxo-3-methyl-3-phenoxybutylphosphonate. For this purpose, 2-methyl-2-phenoxypropionyl chloride is made by reaction of 2-methyl-2-phenoxypropionic acid (50 g.) with thionyl chloride (82 g.), first at about 25° C., then on a steam bath, finally pumping off excess thionyl chloride with addition of toluene.

A solution of dimethyl methylphosphonate (69.5 g.) in 700 ml. of tetrahydrofuran is cooled to b $-75°$ C. under nitrogen and n-butyllithium (355 ml. of 1.6 molar solution in hexane) is added, keeping the temperature below $-55°$ C. The mixture is stirred for 10 min. and to it is slowly added a solution of the 2-methyl-2-phenoxypropionyl chloride above in 50 ml. of tetrahydrofuran, again keeping the temperature below $-55°$ C. The reaction mixture is stirred at $-75°$ C. for 2 hrs., then at about 25° C. for 16 hrs. The mixture is acidified with acetic acid (25 ml.), and the supernatant liquid is concentrated under reduced pressure. The residue is partitioned between water and dichloromethanediethyl ether (3:1). The organic phase is washed with brine, then with saturated sodium bicarbonate, dried over sodium sulfate, and concentrated. Further treatment by silica gel chromatography yields 55 g.; NMR peaks at 6.74–7.4, 3.85, 3.65, 3.56, 3.21 and 1.45 (singlet) $\delta$.

b. Following the procedures of Example 1, steps b and c, but utilizing the above phosphonate instead of the dimethyl 3-phenoxyacetonylphosphonate of that example, there is obtained the corresponding formula-XXIX intermediate, i.e. 3$\alpha$-benzoyl-5$\alpha$-hydroxy-2$\beta$-(3-oxo-4-methyl-4-phenoxy-trans-1-pentenyl)-1$\alpha$-cyclopentaneacetic acid, $\gamma$-lactone, 12.7 g.; m.p. 145°-147° C. (recrystallized from diethyl ether-pentane); NMR peaks at 6.62-7.65, 4.80, 5.46, 1.45, and 1.48 $\delta$.

c. Following the procedure of Example 2, but utilizing the above formula-XXIX compound instead of the formula-XXIX compound of that example, there are obtained the corresponding formula-XXX $\alpha$- and $\beta$-hydroxy isomers, i.e. 3$\alpha$-benzoyloxy-5$\alpha$-hydroxy-2$\beta$-(3$\alpha$-hydroxy-4-methyl-4-phenoxy-trans-1-pentenyl)-1$\alpha$- cyclopentaneacetic acid, γ-lactone, 7.7 g., m.p. 121°–122° C.; NMR peaks at 7.90–8.25, 6.95–7.74, 5.85–5.95, 4.19–4.3, and 1.15 (singlet) δ; and 3α-benzoyloxy-5α-hydroxy-2β-(3β-hydroxy-4-methyl-4-phenoxy-trans-1-pentenyl)-1α-cyclopentaneacetic acid, γ-lactone, 3.65 g., having similar NMR peaks.

d. Following the procedures of Example 3, the 3α-hydroxy intermediate of step c above (8.54 g.) is transformed first to the formula-XXXI benzoyloxy-free compound, i.e. 3α,5α-dihydroxy-2β-(3α-hydroxy-4-methyl-4-phenoxy-trans-1-pentenyl)-1α-cyclopentaneacetic acid, γ-lactone, 6.18 g.; m.p. 65°–66° C.; NMR peaks at 6.86–7.40, 5.62–5.73, 3.47 (singlet) and 1.18 (singlet) δ. Next the corresponding formula-XXXII bis(tetrahydropyranyl) ether is prepared following the procedure of Example 3-b; yield 8.8 g.; infrared absorption spectrum free of hydroxyl absorption at 3300 cm$^{-1}$. Then the formula-XXXIII lactol is prepared following the procedure of Example 3-c; yield of 3α,5α-dihydroxy-2β-(3α-hydroxyl-4-methyl-4-phenoxy-trans-1-pentenyl)-1α-cyclopentaneacetaldehyde, γ-lactol, bis(tetrahydropyranyl) ether, 9.16 g.; infrared absorption spectrum free of γ-lactone absorption at 1760 cm$^{-1}$.

e. Following the procedures of Example 4, the lactol of step d above is transformed by the Wittig reaction, starting with 4 carboxybutyltriphenylphosphonium bromide, to the corresponding formula-XXXIV bis(tetrahydropyranyl) ether of the title compound, yield 7.6 g.; NMR peaks at 7.1–7.3, 6.4 (singlet), 5.3–5.82, 4.6–5.0, and 3.3–4.3 δ.

f. A solution of the formula-XXXIV bis(tetrahydropyranyl) ether of step e above (2.4 g.) in 50 ml. of acetic acid and 25 ml. of water is stirred at about 25° C. for 16 hrs. and then at 37°–39° C. for 1.5 hrs. The product is freeze-dried and then chromatographed on silica gel, eluting with 0–3% methanol in ethyl acetate. Those fractions shown by TLC to contain the product free of starting material and impurities are combined and concentrated to yield the title compound, 0.60 g.; mass spectral peaks (trimethylsilyl derivative) at 706, 691, 613, 601, 571 and 481; NMR peaks at 6.95–7.45, 5.6–5.8, 5.0–5.6, and 3.4–5.0 δ.

EXAMPLE 8

16-Methyl-16-phenoxy-18,19,20-trinor-PGE$_2$ (Formula XIII: g is 3, M is

R$_1$ is hydrogen, R$_2$ and R$_3$ are methyl, and s is zero)

Refer to Chart C. A solution of the formula-XXIV 16-methyl-16-phenoxy-18,19,20-trinor-PGF$_{2\alpha}$, 11,15-bis(tetrahydropyranyl) ether (Example 73, 5.2 g.) in 100 ml. of acetone is cooled to about −20° C. and to it is added slowly 5 ml. of Jones reagent. The mixture is stirred for 15 min., diluted with 600 ml. of ethyl acetate and 600 ml. of diethyl ether, and washed with dilute hydrochloric acid and brine, then dried over magnesium sulfate and concentrated under reduced pressure to an oil.

The above oil, which is the formula-XXXVII bis(tetrahydropyranyl) ether of the title compound, is dissolved in 80 ml. of acetic acid and 40 ml. of water and stirred at 40° C. for 2.5–3 hrs. The product is freeze dried and then chromatographed on silica gel, eluting with 0.75–1.5% methanol in ethyl acetate. Those fractions shown by TLC to contain the product free of starting material and impurities are combined and concentrated to yield the title compound, 2.0 g.; infrared absorption bonds at 2700–3500, 1750, 1715, 1600, and 1500 cm$^{-1}$; NMR peaks at 6.87–7.4, 6.35, 5.6–5.87, 5.2–5.5, 3.8–4.3 δ; mass spectral peaks (trimethylsilyl derivative) at 632, 617, 539, 527, and 497.

Following the procedures of Example 8, each of the bis(tetrahydropyranyl)ethers corresponding to formula XXXIV described following Example 5 is transformed to the corresponding 16-phenoxy (or substituted-phenoxy)-PGE$_2$ type compound or its racemic mixtures, for example 16-phenoxy-17,18,19,20-tetranor-PGE$_2$
16-phenoxy-2,17,18,19,20-pentanor-PGE$_2$
dl-16-phenoxy-17,18,19,20-tetranor-PGE$_2$ and
dl-16-phenoxy-2,17,18,19,20-pentanor-PGE$_2$.

From the 15β-epimers are obtained the corresponding 15β-PGE$_2$ type epimers, for example 16-phenoxy-17,18,19,20-tetranor-15β-PGE$_2$ and
dl-16-phenoxy-17,18,19,20-tetranor-15β-PGE$_2$.

As in Example 8, there is first obtained the bis(tetrahydropyranyl) ether of the PGE$_2$ type compound in each instance.

EXAMPLE 9

16-Methyl-16-phenoxy-18,19,20-trinor-PGE$_2$, Methyl Ester (Formula XIII: g is 3; M is

R$_1$, R$_2$, and R$_3$ are methyl; and s is zero), and 16-Methyl-16-phenoxy-18,19,20-trinor-PGA$_2$, Methyl Ester (Formula XVI: g is 3; M is

R$_1$, R$_2$, and R$_3$ are methyl; and s is zero).

Refer to Chart C.

a. Following the procedure of Example 6a, and using the product of Example 7e above, there is first prepared the formula-XXXVI methyl ester of 16-methyl-16-phenoxy-18,19,20-trinor-PGF$_{2\alpha}$, 11,15-bis-(tetrahydropyranyl) ether, in quantitative yield, having R$_f$=0.8 on silica gel (using as TLC solvent system the organic phase from 500 ml. ethyl acetate, 5 ml. methanol, and 50 ml. water well-shaken).

b. Following the procedure of Example 6b, the methyl ester of part a, above, (9.8 g.) is oxidized with Jones reagent to the corresponding PGE$_2$-type product.

c. The formula-XXXVII 16-methyl-16-phenoxy-18,19,20-trinor-PGE$_2$, 11,15-bis(tetrahydropyranyl) ether, methyl ester of part b above is taken up in 210 ml. of acetic acid, 105 ml. of water, and 35 ml. of tetrahydrofuran. The solution is stirred at 40°–45° C. for 4 hrs., then freeze-dried. The residue is taken up in diethyl ether, washed with cold, dilute sodium bicarbonte solution, dried, and concentrated to a mixture of the title compound, 6.2 g.

d. The mixture from part c is chromatographed on silica gel (800 g.) wet packed in ethyl acetate-hexane (1:1). The column is eluted in 60 ml. fractions with the following solvent mixtures: fractions 1-20, 60% ethyl acetate-40% hexane; fractions 21-40, 70% ethyl acetate-30% hexane; fractions 41-60, 80% ethyl acetate-20% hexane; fractions 61-80, ethyl acetate; fractions 81-100, 2% methanol in ethyl acetate. Fractions 34-44 yield the formula-XVI PGA$_2$-type title compound, 0.48 g.; NMR peaks at 7.56, 7.52, 7.48, 7.44, 6.24, 6.20, 6.14, 6.10, 7.31-6.86, 5.82-5.65, 5.48-5.30, 3.63 (singlet) and 1.28 (singlet) δ; mass spectral peaks (trimethylsilyl derivative) at 484, 453, 451, 407, 391, 350, 260, and 135. Fractions 73-100 yield the formula-XIII PGE$_2$-type title compound, 3.0 g.; NMR peaks at 7.30-6.87, 5.82-5.65, 5.48-5.30, 3.64 (singlet), 1.25, and 1.21 δ; mass spectral peaks (trimethylsilyl derivative) at 574, 543, 484, 481, 469, 439, 391, and 135.

EXAMPLE 10

16-Methyl-16-phenoxy-18,19,20-trinor-PGF$_{2\alpha}$, Methyl Ester (Formula XIV: g is 3; M is

R$_1$, R$_2$, and R$_3$ are methyl; s is zero; and ~ is alpha)

A solution of 16-methyl-16-phenoxy-18,19,20-trinor-PGF$_{2\alpha}$, 11,15-bis(tetrahydropyranyl) ether, methyl ester (Example 9a, 4.0 g.) in 90 ml. of acetic acid, 45 ml. of water and 15 ml. of tetrahydrofuran is stirred at 40°-45° C. for 4 hrs. The reaction mixture is diluted with 150 ml. of water, frozen, and lyophilized. The residue is taken up in ether and washed with ice-cold dilute sodium bicarbonate solution. The organic phase is dried over sodium sulfate and concentrated under reduced pressure. The residue is chromatographed on silica gel, eluting with 0-20% methanol in ethyl acetate. Those fractions shown by TLC to contain the product free of starting material and impurities are combined and concentrated to yield the title compound, 2.08 g.; NMR peaks at 7.38-6.86, 5.72-5.62, 5.50-5.28, 3.66 (singlet), and 1.22 (singlet) δ; mass spectral peaks (trimethylsilyl derivative) at 633, 617, 555, 513, 423, and 135.

EXAMPLE 11

16-Methyl-16-phenoxy-18,19,20-trinor-PGF$_{2\beta}$ (Formula XV: g is 3; M is

R$_1$ is hydrogen; R$_2$, and R$_3$ are methyl; and s is zero)

Refer to Chart D. A solution of sodium borohydride (300 mg.) in 6 ml. of ice-cold methanol is added to a solution of 16-methyl-16-phenoxy-18,19,20-trinor-PGE$_2$ (Example 8, 650 mg.) in 30 ml. of methanol at −5° C. The mixture is stirred for an additional 5 min., made slightly acidic with acetic acid, and concentrated under reduced pressure. The residue is extracted with dichloromethane and the organic phase is washed with water, dilute aqueous sodium bicarbonate, and brine, then dried over sodium sulfate and concentrated under reduced pressure. This residue is chromatographed over silica gel, eluting with 0-10% ethanol in ethyl acetate. Those fractions containing the title compound free of starting material and impurities, as shown by TLC, are combined and concentrated to yield the formula-XV title compound. In other fractions the corresponding formula XIV PGF$_{2\alpha}$-type compound is obtained.

Following the procedure of Example 11, each of the 16-phenoxy (or substituted-phenoxy)-PGE$_2$ type compounds, their 15β epimers, and racemates described following Example 8 is transformed to the corresponding 16-phenoxy (or substituted-phenoxy)-PGF$_{2\beta}$ type compound or 15β epimer or racemic mixture. There are also obtained the corresponding PGF$_{2\alpha}$-type compounds.

EXAMPLE 12

16-Phenoxy-17,18,19,20-tetranor-PGA$_2$ (Formula XVI: g is 3; M is

R$_1$, R$_2$, and R$_3$ are hydrogen; and s is zero)

Refer to Chart D. A solution of 16-phenoxy-17,18,19,20-tetranor-PGE$_2$ methyl ester (Example 6, 300 mg.), 4 ml. of tetrahydrofuran and 4 ml. of 0.5 N. hydrochloric acid is left standing at 25° C. for 5 days. Brine and dichloromethane-ether (1:3) are added and the mixture is stirred. The organic phase is separated, dried, and concentrated. The residue is dissolved in diethyl ether and the solution is extracted with saturated aqueous sodium bicarbonate. The aqueous phase is acidified with dilute hydrochloric acid and then extracted with dichloromethane. This extract is dried and concentrated to yield the formula-XVI title compound.

Following the procedure of Example 12, each of the 16-phenoxy (or substituted-phenoxy)-PGE$_2$ type compounds, 15β epimers, and racemates, described following Example 8 is transformed to the corresponding 16-phenoxy (or substituted-phenoxy)-PGA$_2$ type compound or 15β epimer or racemic mixture.

EXAMPLE 13

16-Phenoxy-17,18,19,20-tetranor-PGB$_2$ (Formula XVII: g is 3; M is

R$_1$, R$_2$, and R$_3$ are hydrogen; and s is zero)

Refer to Chart D. A solution of 16-phenoxy-17,18,19,20-tetranor-PGE$_2$ methyl ester (Example 6, 200 mg.) in 100 ml. of 50% aqueous ethanol containing about one gram of potassium hydroxide is kept at 25° C. for 10 hrs. under nitrogen. The solution is then cooled to 10° C. and neutralized by addition of 3N. hydrochloric acid at 10° C. The resulting solution is extracted repeatedly with ethyl acetate, and the combined ethyl acetate extracts are washed with water and then with brine, dried, and concentrated to yield the formula-XVII title compound.

Following the procedure of Example 13, each of the 16-phenoxy (or substituted-phenoxy)-PGE$_2$ type compounds, their 15$\beta$ epimers, and racemates, described following Example 8 is transformed to the corresponding 16-phenoxy (or substituted-phenoxy)-PGB$_2$ type compound or 15$\beta$ epimer or racemic mixture.

EXAMPLE 14

16-Methyl-16-Phenoxy-18,19,20-trinor-PGE$_1$ (Formula VIII: g is 3; M is

R$_1$ is hydrogen; R$_2$ and R$_3$ are methyl; and s is zero) and 16-Methyl-16-Phenoxy-18,19,20-trinor-13,14-dihydro-PGE$_1$ (Formula XVIII: g is 3; M is

R$_1$ is hydrogen; R$_2$ and R$_3$ are methyl; and s is zero)

A mixture of the formula-XXXVII bis(tetrahydropyranyl) ether of 16-methyl-16-phenoxy-18,19,20-trinor-PGE$_2$ (Example 8, 220 mg.), 5% rhodium-on-alumina catalyst (40 mg.), and 16 ml. of ethyl acetate is stirred under one atmosphere of hydrogen at about 0° C. until substantially all of the starting material has been used, as shown by TLC. The mixture is filtered to remove catalyst, and the filtrate is concentrated. The residue is dissolved in 1 ml. of tetrahydrofuran and 6 ml. of 66% acetic acid and the mixture is warmed to 50° C. for 2.5 hrs. The mixture is concentrated under reduced pressure and the residue is chromatographed over silica gel, eluting with the upper layer of a mixture of ethyl acetate-acetic acid-Skellysolve B (isomeric hexanes)-water (90:20:50:100). Those fractions shown by TLC to contain the title compounds free of starting material and impurities are combined and concentrated to yield the title compounds.

Following the procedure of Example 14, each of the PGE$_2$-type bis(tetrahydropyranyl) ethers described following Example 8 is transformed to the corresponding 16-phenoxy (or substituted-phenoxy)-PGE$_1$ type or 13,14-dihydro-PGE$_1$ type compound, 15$\beta$ epimer, or racemate.

EXAMPLE 15

16-Phenoxy-17,18,19,20-tetranor-13,14-dihydro-PGE$_1$ Methyl Ester (Formula XVIII: g is 3; M is

R$_1$ is methyl; R$_2$ and R$_3$ are hydrogen; and s is zero)

A solution of 16-phenoxy-17,18,19,20-tetranor-PGE$_2$ methyl ester (Example 6, 100 mg.) in 10 ml. of ethyl acetate is shaken with hydrogen at about one atmosphere pressure at 25° C. in the presence of a 5% palladium-on-charcoal catalyst (15 mg.). Two equivalents of hydrogen are used, whereupon the hydrogenation is stopped and the catalyst is removed by filtration. The filtrate is concentrated under reduced pressure and the residue is chromatographed on silica gel, eluting with ethyl acetate-Skellysolve B (isomeric hexanes) ranging from 50–100% ethyl acetate. Those fractions shown by TLC to contain the desired product free of starting material and impurities are combined and concentrated to give the title compound.

Following the procedures of Examples 11, 12, and 13, each of the 16-phenoxy (or substituted-phenoxy)-PGE$_1$ type or 13,14-dihydro-PGE$_1$ type compounds, 15$\beta$ epimers or racemates described in and following Examples 14 and 15 is transformed respectively to the corresponding 16-phenoxy (or substituted-phenoxy)-PGF$_{1\alpha}$, -PGF$_{1\beta}$, -PGA$_1$, or PGB$_1$ type or 16-phenoxy (or substituted-phenoxy)-13,14-dihydro-PGF$_{1\alpha}$, -PGF$_{1\beta}$, -PGA$_1$, or -PGB$_1$ type compound, 15$\beta$ epimer or racemate.

EXAMPLE 16

16-Phenoxy-17,18,19,20-tetranor-PGF$_{2\alpha}$ Methyl Ester (Formula XIV: g is 3, M is

R$_1$ is methyl, R$_2$ and R$_3$ are hydrogen, s is zero and ~ is alpha)

A solution of diazomethane (about 0.5 g.) in 25 ml. of diethyl ether is added to a solution of 16-phenoxy-17,18,19,20-tetranor-PGF$_{2\alpha}$ (Example 5, 50 mg.) in 25 ml. of a mixture of methanol and diethyl ether (1:1). After the mixture has stood at about 25° C. for 5 min., it is concentrated under reduced pressure to yield the title compound.

Following the procedure of Example 16, each of the other 16-phenoxy (or substituted-phenoxy)-PGF-type, PGE-type, PGA-type, and PGB-type free acids and also their 15$\beta$-epimers and racemates defined above is converted to the corresponding methyl ester.

Likewise following the procedure of Example 16, but replacing diazomethane with diazoethane, diazobutane, 1-diazo-2-ethylhexane, and diazodecane, there are obtained the corresponding ethyl, butyl, γ-ethylhexyl, and decyl esters of 16-phenoxy-17,18,19,20-tetranor-PGF$_{2\alpha}$. In the same manner, each of the other 16-phenoxy (or substituted-phenoxy)-PGF-type, PGE-type, PGA-type, and PGB-type free acids and also their 15$\beta$-epimers and racemates defined above is converted to the corresponding ethyl, butyl, 2-ethylhexyl, and decyl esters.

EXAMPLE 17

16-Phenoxy-17,18,19,20-tetranor-PGF$_{2\alpha}$ Sodium Salt

A solution of 16-phenoxy-17,18,19,20-tetranor-PGF$_{2\alpha}$ (Example 5, 100 mg.) in 50 ml. of a water-ethanol mixture (1:1) is cooled to 5° C. and neutralized with an equivalent amount of 0.1 N. aqueous sodium hydroxide solution. The neutral solution is concentrated to a residue of the title compound.

Following the procedure of Example 17 but using potassium hydroxide, calcium hydroxide, tetramethylammonium hydroxide, and benzyltrimethylammonium hydroxide in place of sodium hydroxide, there are obtained the corresponding salts of 16-phenoxy-17,18,19,20-tetranor-PGF$_{2\alpha}$.

Likewise following the procedure of Example 17 each of the 16-phenoxy (or substituted-phenoxy) PGE-type, PGF-type, PGA-type, and PGB-type acid and also their 15β-epimers and racemates defined above is transformed to the sodium, potassium, calcium, tetramethylammonium, and benzyltrimethylammonium salts.

I claim:

1. An optically active compound of the formula

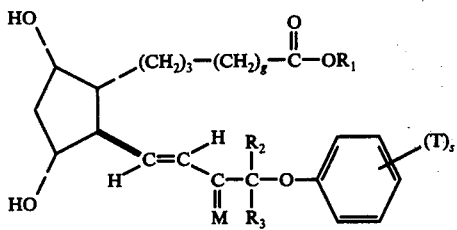

or a racemic compound of that formula and the mirror image thereof, wherein $g$ is an integer from 2 to 5, inclusive; wherein M is

wherein $R_1$ is hydrogen or alkyl of one to 12 carbon atoms, inclusive, cycloalkyl of 3 to 10 carbon atoms, inclusive, aralkyl of 7 to 12 carbon atoms, inclusive, phenyl, or phenyl substituted with one, 2, or 3 chloro or alkyl of one to 4 carbon atoms, inclusive; wherein $R_2$ and $R_3$ are hydrogen, methyl, or ethyl; wherein T is alkyl of one to 3 carbon atoms, inclusive, fluoro, chloro, trifluoromethyl, or —OR$_4$ wherein R$_4$ is alkyl of one to 3 carbon atoms, inclusive, and wherein $s$ is zero, one, 2, or 3, with the proviso that not more than two T's are other than alkyl; including each of the lower trialkanoates thereof, and each of the pharmacologically acceptable salts thereof when $R_1$ is hydrogen.

2. A compound according to claim 1 wherein "g" is 3.

3. A compound according to claim 2 wherein "M" is

4. A compound according to claim 3 wherein both $R_2$ and $R_3$ are hydrogen.

5. 16-Phenoxy-17,18,19,20-tetranor-PGF$_{1\alpha}$, a compound according to claim 4.

6. A compound according to claim 4 wherein "T" is trifluoromethyl and "s" is one.

7. A compound according to claim 3 wherein one or both $R_2$ and $R_3$ are methyl.

8. 16-Methyl-16-phenoxy-18,19,20-trinor-PGF$_{1\alpha}$, a compound according to claim 7.

9. A compound according to claim 7 wherein "T" is trifluoromethyl and "s" is one.

10. 16-Methyl-16-phenoxy-2a,2b-dihomo-18,19,20-trinor-PGF$_{1\alpha}$, a compound according to claim 1.

* * * * *